(12) United States Patent
Watanabe

(10) Patent No.: US 8,052,972 B2
(45) Date of Patent: *Nov. 8, 2011

(54) REMEDIES FOR INFLAMMATORY BOWEL DISEASES

(75) Inventor: Mamoru Watanabe, Tokyo (JP)

(73) Assignee: Japan Tobacco, Inc., Tokyo (JP)

( * ) Notice: Subject to any disclaimer, the term of this patent is extended or adjusted under 35 U.S.C. 154(b) by 84 days.

This patent is subject to a terminal disclaimer.

(21) Appl. No.: 12/268,882

(22) Filed: Nov. 11, 2008

(65) Prior Publication Data

US 2009/0155273 A1 Jun. 18, 2009

Related U.S. Application Data

(63) Continuation of application No. 10/472,743, filed as application No. PCT/JP02/01361 on Feb. 18, 2002, now Pat. No. 7,465,444.

(30) Foreign Application Priority Data

Mar. 27, 2001 (JP) ................................. 2001-089158
Jan. 29, 2002 (JP) ................................. 2002-019291

(51) Int. Cl.
*A61K 39/395* (2006.01)
(52) U.S. Cl. .................................................... 424/130.1
(58) Field of Classification Search .................... None
See application file for complete search history.

(56) References Cited

U.S. PATENT DOCUMENTS

| | | | |
|---|---|---|---|
| 5,484,892 | A | 1/1996 | Tedder et al. |
| 5,506,126 | A | 4/1996 | Seed et al. |
| 5,521,288 | A | 5/1996 | Linsley et al. |
| 5,747,461 | A | 5/1998 | Markov |
| 5,770,197 | A | 6/1998 | Linsley et al. |
| 5,914,112 | A | 6/1999 | Bednar et al. |
| 6,075,181 | A | 6/2000 | Kucherlapati et al. |
| 6,531,505 | B2 | 3/2003 | Xu et al. |
| 6,803,039 | B2 | 10/2004 | Tsuji et al. |
| 7,030,225 | B1 | 4/2006 | Tamatani et al. |
| 7,045,615 | B2 | 5/2006 | Tamatani et al. |
| 7,112,655 | B1 | 9/2006 | Tamatani et al. |
| 7,125,551 | B2 | 10/2006 | Kroczek |
| 7,132,099 | B2 | 11/2006 | Kroczek |
| 7,166,283 | B2 | 1/2007 | Tsuji et al. |
| 7,196,175 | B2 | 3/2007 | Tamatani et al. |
| 7,217,792 | B2 | 5/2007 | Tamatani et al. |
| 7,226,909 | B2 | 6/2007 | Tamatani et al. |
| 7,247,612 | B2 | 7/2007 | Tamatani et al. |
| 7,259,147 | B2 | 8/2007 | Tamatani et al. |
| 7,259,247 | B1 | 8/2007 | Kroczek |
| 7,279,560 | B2 | 10/2007 | Tamatani et al. |
| 7,294,473 | B2 | 11/2007 | Tamatani et al. |
| 7,438,905 | B2 | 10/2008 | Suzuki et al. |
| 7,465,444 | B2 * | 12/2008 | Watanabe .................. 424/130.1 |
| 2002/0151685 | A1 | 10/2002 | Tamatani et al. |
| 2002/0156242 | A1 | 10/2002 | Tamatani et al. |
| 2002/0164697 | A1 | 11/2002 | Coyle et al. |
| 2003/0083472 | A1 | 5/2003 | Tamatani et al. |
| 2004/0131608 | A1 | 7/2004 | Watanabe |
| 2004/0229790 | A1 | 11/2004 | Tezuka et al. |
| 2006/0140944 | A1 | 6/2006 | Yoshinaga et al. |

FOREIGN PATENT DOCUMENTS

| | | |
|---|---|---|
| AU | 752433 | 4/1999 |
| DE | 19821060 | 4/1999 |
| EP | 0 984 023 | 3/2000 |
| EP | 1 125 585 | 8/2001 |
| JP | 5-72204 | 3/1993 |
| JP | 11-228442 | 8/1999 |
| JP | 2000-154151 | 6/2000 |
| WO | WO 95/33770 | 12/1995 |
| WO | WO 97/26912 | 7/1997 |
| WO | WO 98/11909 | 3/1998 |
| WO | WO 98/19706 | 5/1998 |
| WO | WO 98/37415 | 8/1998 |
| WO | WO 98/38216 | 9/1998 |
| WO | WO 98/45331 | 10/1998 |
| WO | WO 99/15553 | 4/1999 |
| WO | WO 00/19988 | 4/2000 |
| WO | WO 00/46240 | 8/2000 |
| WO | WO 00/67788 | 11/2000 |
| WO | WO 01/08700 | 2/2001 |
| WO | WO 01/12658 | 2/2001 |
| WO | WO 01/15732 | 3/2001 |
| WO | WO 01/18022 | 3/2001 |
| WO | WO 01/21796 | 3/2001 |
| WO | WO 01/32675 | 5/2001 |
| WO | WO 02/44364 | 6/2001 |
| WO | WO 01/64704 | 9/2001 |
| WO | WO 01/87981 | 11/2001 |
| WO | WO 02/070010 | 9/2002 |
| WO | WO 02/076504 | 10/2002 |

OTHER PUBLICATIONS

Carlesso et al., "Depletion of inducible co-stimulator (ICOS) bearing T cells inhibits expansion of T follicular helper cells ($T_{FH}$) and prevents disease in a graft versus host mouse model of scleroderma" Poster Presentation, American College of Rheumatology, 2009 Annual Scientific Meeting, Oct. 19, 2009.

Carlesso et al., "Targeted depletion of inducible co-stimulator (ICOS) bearing I cells prevents disease in a graft versus host model of scleroderma" Poster Presentation, 9th International Conference on Systemic Lupus Erythematosus, Jun. 25, 2010.

Cook et al., "The human immunoglobulin $V_H$ repertoire," *Immunology Today* (1995) 16(5):237-42.

Faggioni et al., "Determination of the minimum anticipated biological level (MABEL) for an ADCC-enhanced inducible co-stimulator (ICOS) monoclonal antibody for the treatment of autoimmune diseases" Poster Presentation, Annual Congress of the European League Against Rheumatism, Jun. 2010.

Ghosh et al. "Ulcerative colitis" (2000) BMJ. 320(7242):1119-23.

Hanauer et al. "Management of Crohn's disease in adults" (2001) Am J Gastroenterol. 96(3):635-43.

Koh et al., "A screening method of SH2 domain ligands and blockers using a solid phase binding" (1997) Cancer Lett. 120(1):1-7.

(Continued)

*Primary Examiner* — Ilia Ouspenski

(74) *Attorney, Agent, or Firm* — Fish & Richardson P.C.

(57) ABSTRACT

Antibodies against AILIM (also called ICOS and 8F4) were found to significantly suppress the onset of inflammatory bowel diseases (especially Crohn's disease and colitis (ulcerative colitis and such)), and exhibit a significant therapeutic effect against inflammatory bowel diseases.

21 Claims, 12 Drawing Sheets

OTHER PUBLICATIONS

Mendez et al. "Functional transplant of megabase human immunoglobulin loci recapitulates human antibody response in mice" (1997) Nat Genet. 15(2):146-56.

Mittereder et al., "ICOS is critical for follicular helper T cells ($T_{FH}$)-mediated maintenance of germinal center B cells in non human primates" Poster Presentation, American College of Rheumatology, 2008 Annual Scientific Meeting, Oct. 28, 2008.

Mittereder, "ICOS is critical for T follicular helper cell-mediated maintenance of germinal center B cells in non-human primates" FASEB Summer Research Conference—Autoimmunity, Jul. 2, 2009.

Soderlind et al., "Domain libraries: Synthetic diversity for de novo design of antibody V-regions," *Gene* (1995) 160(2):269-72.

Takai et al. "Epitope analysis and primary structures of variable regions of anti-human FcepsilonRI monoclonal antibodies, and expression of the chimeric antibodies fused with human constant regions" Biosci Biotechnol Biochem. (2000) 64(9):1856-67.

Taylor et al. "Unraveling Functions of ICOS Bearing T Cells: New Insights about Treating Autoimmune Disorders" Poster Presentation, Keystone Symposia on Tolerance and Autoimmunity, Feb. 21-26, 2010.

van der Merwe et al., "CD80 (B7-1) binds both CD28 and CTLA-4 with a low affinity and very fast kinetics," *Journal of Experimental Medicine* (1997) 185(3):393-403.

Abbas, "T-cell stimulation: an abundance of B7s," Nat Med. 5(12):1345-6 (1999).

Aicher et al., "Characterization of human inducible costimulator ligand expression and function," J. of Immunology 164:4689-4696 (2000).

Akbari et al., "Antigen-specific regulatory T cells develop via the ICOS-ICOS-ligand pathway and inhibit allergen-induced airway hyperreactivity," Nature Medicine 8(9):1024-1032 (2002).

Andersen et al., "Allelic variation of the inducible costimulator (ICOS) gene: detection of polymorphisms, analysis of the promoter region, and extended haplotype estimation," Tissue Antigens 61:276-285 (2003).

Ara et al., "Potent activity of soluble B7RP-1-FC in therapy of murine tumors in syngeneic hosts," Int. J. Cancer 103:501-507 (2003).

Arimura et al., "A co-stimulatory molecule on activated T cells, H4/ICOS, delivers specific signals in $T_h$ cells and regulates their responses," International Immunology 14(6):555-566 (2002).

Atwood T., Science 2000, 290:471-473.

Bajorath, "A molecular model of inducible costimulator protein and three-dimensional analysis of its relation to the CD28 family of T cell-specific costimulatory receptors," J. Mol. Model 5:169-176 (1999).

Beier et al., "Induction, binding specificity and function of human ICOS," Eur. J. Immunol. 30:3707-3717 (2000).

Bensimon et al., "Human lupus anti-DNA autoantibodies undergo essentially primary V kappa gene rearrangements," EMBO J. 13(13):2951-62 (1994).

Bennett et al., "Program death-1 engagement upon TCR activation has distinct effects on costimulation and cytokine-driven proliferation: Attenuation of ICOS, IL-4, and IL-21, but not CD28, IL-7, and IL-15 responses" J. of Immunol. 170:711-718 (2003).

Bertram et al., "Role of ICOS versus CD28 in antiviral immunity," Eur. J. Immunol. 32:3376-3385 (2002).

Biancone et al., "Lymphocyte costimulatory receptors in renal disease and transplantation," J. Nephrol 15:7-16 (2002).

Bonhagen et al., "ICOS$^+$ Th cells produce distinct cytokines in different mucosal immune responses," Eur. J. Immunol. 33:392-401 (2003).

Brodie et al., "LICOS, a primordial costimulatory ligand?" Current Biology 10(6):333-336 (2000).

Buonfiglio et al., "Characterization of a novel human surface molecule selectively expressed by mature thymocytes, activated T cells and subsets of T cell lymphomas," Eur. J. Immunol. 29:2863-2874 (1999).

Buonfiglio et al., "The T cell activation molecule H4 and the CD28-like molecule ICOS are identical," Eur. J. Immunol. 30:3463-3467 (2000).

Cameron "Recent advances in transgenic technology" Molecular Biotechnology 7:253-65 (1997).

Campbell et al., "Separable effector T cell populations specialized for B cell help or tissue inflammation," Nat Immunol. 2(9):876-81 (2001).

Carreno et al., "The B7 family of ligands and its receptors," Annu. Rev. Immunol. 20:29-53 (2000).

Chambers, "The expanding world of co-stimulation: the two-signal model revisited," Trends in Immunology 22(4):217-223 (2001).

Chapoval et al., "B7-H3: a costimulatory molecule for T cell activation and IFN-gamma production," Nat Immunol. 2(3):269-74 (2001).

Cocks et al., "A novel receptor involved in T-cell activation," Nature, 376:260-263 (1995).

Coyle et al., "The CD28-related molecule ICOS is required for effective T cell-dependent immune responses," Immunity 13:95-105 (2000).

Deng et al., "Critical role of CD81 in cognate T-B cell interactions leading to $T^h2$ responses," International Immunology 14(5):513-523 (2002).

Dong et al., "B7-H1, a third member of the B7 family, co-stimulates T-cell proliferation and interleukin-10 secretion," Nat. Med. 5(12):1365-9 (1999).

Dong et al., "Cutting Edge: Critical role of inducible costimulator in germinal center reactions" The J. Immunol. 166:3659-3662 (2001).

Dong et al., "ICOS co-stimulatory receptor is essential for T-cell activation and function," Nature 409:97-101 (2001).

Eljaschewitsch et al., "Identification of a novel activation antigen on human CD4+ T cells," Immunobiol., 194(1-3):27 (1995).

Feito et al., "Mechanisms of H4/ICOS costimulation: effects on proximal TCR signals and MAP kinase pathways," Eur. J. Immunol. 33:204-214 (2003).

Flesch, "Inducible costimulator (ICOS)," J. of Biol. Regul.Homeost. Agents 16:214-216 (2002)-.

Flesch, "Inducible costimulator-ligand (ICOS-L)," J. of Biol. Regul. Homeost. Agents 16:217-219 (2002).

Frauwirth et al., "Activation and inhibition of lymphocytes by costimulation," J. of Clin. Invest. 109(3):295-299 (2002).

Fujisawa et al., "Presence of high contents of thymus and activation-regulated . . . dermatitis," J. Allergy of Clin. Immunol. 110(1):139-146 (2002).

Goding, "Monoclonal Antibodies: Principles and Practice," $2^{nd}$ Edition, Academic Press, Orlando, Florida, Chapter 8, pp. 281-293 (1986).

Goni et al., "Structural and idiotypic characterization of the L chains of human IgM autoantibodies with different specificities," J. Immunol. 142(9):3158-63 (1989).

Gonzalo et al., "Cutting edge: The related molecules CD28 inducible costimulator deliver both unique and complementary signals required for optimal T cell activation," J. of Immunol. 166:1-5 (2001).

Gonzalo et al., "ICOS is critical for T helper cell-mediated lung mucosal inflammatory responses," Nat Immunol. 2(7):597-604 (2001).

Greenwald et al., "Cutting edge: Inducible costimulator protein regulates both Th1 and Th2 responses to cutaneous leishmaniasis," J. of Immunol. 168:991-995 (2002).

Greenwald et al., "Negative co-receptors on lymphocytes," Current Opinion in Immunology 14:391-396 (2002).

Grimbacher et al., "Homozygoud loss of ICOS is associated with adult-onset common variable immunodeficiency," Nature Immunology 4(3):261-268 (2003).

Guo et al., "Stimulatory effects of B7-related protein-1 on cellular and humoral immune responses in mice," J. of Immunol. 166:5578-5584 (2001).

Guo et al., "Prolonged survival in rat liver transplantation with mouse monoclonal antibody against an inducible costimulator (ICOS), " Transplantation 73(7):1027-1032 (2002).

Haimila et al., "Genetic polymorphism of the human ICOS gene," Immunogenetics 53:1028-1032 (2002).

Hanzawa et al., "Characteristics of a TTH1 antibody which blocks an unknown adhesion phenomenon," Proceedings of the Japanese Society for Immunology, vol. 24, Abstract No. W17-13 (1994) [Original Japanese and English Language Translation].

Harada et al., "A single amino acid alteration in cytoplasmic domain determines IL-2 promoter activation by ligation of CD28 but not inducible costimulator (ICOS)," J. Exp. Med. 197(2):257-262 (2003).

Harlow and Lane, "Antibodies: A Laboratory Manual," Cold Spring Harbor Laboratory, p. 285 (1988).

Heyeck et al., "Developmental regulation of a murine T-cell-specific tyrosine kinase gene, Tsk," Proc. Natl. Acad. Sci. USA, 90:669-673 (1993).

Houdebine "Production of pharmaceutical proteins from transgenic animals" J. Biotechnol. 34:269-87 (1994).

Huang Z., Pharmacology and Therapeutics, 2000, 86:201-215.

Hutloff et al., "ICOS is an inducible T-cell co-stimulator structurally and functionally related to CD28," Nature 397:263-266 (1999).

Hutloff et al., "Identification and initial characterization of a novel T cell-specific cell surface activation antigen," Immunobiol., 197(2-4):172 (1997).

Ihara et al., "Association studies of CTLA-4, CD28, and ICOS gene polymorphisms with type 1 diabetes in the Japanese population," Immunogenetics 53(6):447-54 (2001).

Iiyama et al., "The role of inducible co-stimulator (ICOS)/B7-related protein-1 (B7RP-1) interaction in the functional development of Peyer's patches," Immunology Letters, In Press, Uncorrected Proof available online Apr. 11, 2003, http://www.sciencedirect.com/science/journal/01652478.

Ishikawa et al., "Prediction of the Coding Sequences of Unidentified Human Genes. X. The Complete Sequences of 100 New cDNA Clones from Brain Which Can Code for Large Proteins in vitro," DNA Research, 5:169-176 (1998).

Iwai et al., "Amelioration of collagen-induced arthritis by blockade of inducible costimulator-B7 homologous protein costimulation," J. of Immunol. 169:4332-4339 (2002).

Kappel et al. "Regulating gene expression in transgenic animals" Current Opinion in Biotechnology 3:548-53 (1992).

Kanai et al., "ICOS costimulation in inflammatory bowel disease," J. of Gastroenterology 37(14):78-81 (2002).

Kanai et al., "Innate Immunity" 10(1):65-70 (2002).

Khayyamian et al., "ICOS-ligand, expressed on human endothelial cells, costimulates Th1 and Th2 cytokine secretion by memory CD4+ T cells," PNAS 99(9):6198-6203 (2002).

Kopf et al., "Inducible costimulator protein (ICOS) controls T helper cell subset polarization after virus and parasite infection," J. Exp. Med. 192(1):53-61 (2000).

Kosuge et al., "Induction of immunologic tolerance to cardiac allograft by simultaneous blockade of inducible co-stimulator and cytotoxic T-lymphocyte antigen 4 pathway," Transplantation 75(8):1374-1379 (2003).

Kuchroo et al., "B7-1 and B7-2 costimulatory molecules activate differentially the Th1/Th2 developmental pathways: Application to autoimmune disease therapy," Cell, 80:707-718 (1995).

Lamhemedi-Cherradi et al., "Further mapping of the Idd5.1 locus for autoimmune diabetes in NOD mice," Diabetes 50(12):2874-8 (2001).

Lewthwaite et al., Curr. Opin. Infect. Diseases, 2005, 18:427-435.

Liang et al., "Constitutive expression of the B7h ligand for inducible costimulator . . . CD40 signalling," J. Exp. Med. 196(1):97-108 (2002).

Ling et al., "Assembly and annotation of human chromosome 2q33 sequence containing the CD28, CTLA4, and ICOS gene cluster: analysis by computational, comparative, and microarray approaches," Genomics 78(3):155-68 (2001).

Ling et al., "Cutting edge: Identification of GL50, a novel B7-like protein that functionally binds to ICOS receptors," J. of Immunol. 164:1653-1657 (2000).

Ling et al., "Differential expression of inducible costimulator-ligand splice variants: lymphoid regulation of mouse GL50-B and human GL50 molecules," J Immunol. 166(12):7300-8 (2001).

Linsley, "T cell activation: you can't get good help," Nat Immunol. 2(2):139-40 (2001).

Liu et al. "B7H costimulates clonal expansion of, and cognate destruction of tumor cells by, CD8(+) T lymphocytes in vivo," J Exp Med. 194(9):1339-48 (2001).

Lucia et al., "Expression of the novel T cell activation molecule hpH4 in HIV-infected patients: Correlation with disease status", AIDS Research and Human Retroviruses 16(6):549-557 (2000).

Löhning et al., "Expression of ICOS in vivo defines CD4+ effector T cells with high inflammatory potential and a strong bias for secretion of interleukin 10," J. Exp. Med. 197(2):181-193 (2003).

Mackay et al., "Follicular homing T helper (Th) cells and the Th1/Th2 paradigm," J Exp Med. 192(11):F31-4 (2000).

Mages et al., "Molecular cloning and characterization of murine ICOS and identification of B7h as ICOS ligand," Eur. J. Immunol. 30:1040-1047 (2000).

Marguet et al., "cDNA Cloning for Mouse Thymocyte-activating Molecule," The Journal of Biological Chemistry, 267(4):2200-2208 (1992).

Matsui et al., "Adenovirus-mediated gene transfer of ICOSIg fusion protein ameliorates ongoing experimental autoimmune myocarditis," Human Gene Therapy 14:521-532 (2003).

McAdam et al., "ICOS is critical for CD40-mediated antibody class switching," Nature 409:102-104 (2001).

McAdam et al., "Mouse inducible costimulatory molecule (ICOS) expression is enhanced by CD28 costimulation and regulates differentiation of CD+ T cells," J. of Immunol. 165:5035-5040 (2000).

McAdam et al. (2000) "Mouse inducible costimulatory (ICOS) molecule expression is increased by CD28 costimulation and regulates development of Th2 cells," FASEB Journal, 14(6):A1169.

Metzler et al., Nature Structural Biol. 1997, 4:527-531.

Mittrücker et al., "Inducible costimulator protein controls the protective T cell response against $Listeria$ $monocytogenes$," J. of Immunol. 169:5813-5817 (2002).

Mueller et al., "T cells: A proliferation of costimulatory molecules," Current Biol. 10(6):227-230 (2000).

Mullins et al. "Expression of the DBA/2J Ren-2 gene in the adrenal gland of transgenic mice" EMBO J., 8:4065-72 (1989).

Mullins et al. "Fulminant hypertension in transgenic rats harbouring the mouse Ren-2 gene" Nature, 344:541-44 (1990).

Mullins et al. "Transgenesis in nonmurine species" Hypertension 22:630-33 (1993).

Nakamura et al., "Acceptance of islet allografts in the liver of mice by blockade of an inducible costimulator," Transplantation 75(8):1115-1118 (2003).

Niemann "Transgenic farm animals get off the ground" Transgenic Research, 7:73-75 (1998).

Nojima et al., "The 4F9 antigen is a member of the tetra spans transmembrane protein family and functions as an accessory molecule in T cell activation and adhesion," Cellular Immunology, 152:249-260 (1993).

Nurieva et al., "Inducible costimulator is essential for collagen-induced arthritis," J. Clin. Invest. 111(5):701-06 (2003).

Ogasawara et al., "Inducible costimulator costimulates cytotoxic activity and IFN-γ production in activated murine NK cells," J. of Immunol. 169:3676-3685 (2002).

Ogawa et al., "Opposing effects of anti-activation-inducible lymphocyte-immunomodulatory molecule/inducible costimulator antibody on the development of acute versus chronic graft-versus-host disease," J Immunol. 167(10):5741-8 (2001).

Okamoto et al., "Expression and function of the co-stimulator H4/ICOS on activated T cells of patients with rheumatoid arthritis," J. of Rheumatology 30:1157-1163 (2003).

Okazaki et al., "New regulatory co-receptors: inducible co-stimulator and PD-1," Current Opinion on Immunology 14:779-782 (2002).

Overbeek "Factors affecting transgenic animal production," Transgenic Animal Technology, A Laboratory Handbook 96-98 (1994).

Özkaynak et al., "Importance of ICOS-B7RP-1 costimulation in acute and chronic allograft rejection," Nature Immunology 2(7):591-596 (2001).

O'Neill, "Co-stimulating allergy," Trends Immunol. 22(4):183 (2001).

Parry et al., "CD28 and inducible costimulatory protein Src homology 2 binding domains show distinct regulation of phosphatidylinositol 3-kinase, Bcl-$x_L$, and IL-2 expression in primary human CD4 T lymphocytes," J. of Immunol. 171:166-174 (2003).

Pech et al., "A large section of the gene locus encoding human immunoglobulin variable regions of the kappa type is duplicated," J. Mol Biol. 183(3):291-9 (1985).
Poster, Kyoto International Conference Hall, Takaragaike Sakyo-ku, Kyoto, Japan (Nov. 30, 1994) [Original Japanese and English Language Translation].
Pound, "A new T-helper cell subset?" Trends Immunol. 22(4):182-3 (2001).
Redoglia et al., "Characterization of H4: a mouse T lymphocyte activation molecule functionally associated with CD3/T cell receptor," Eur. J. Immunol. 26:2781-2789 (1996).
Richter et al., "Tumor necrosis factor-α regulates the epxpression of inducible costimulator receptor ligand on CD34+ progenitor cells during differentiation into antigen presenting cells," J. of Biological Chem. 276(49):45686-45693 (2001).
Riley et al., "ICOS Costimulation requires IL-2 and can be prevented by CTLA-4 engagement," J. Immunol. 166:4943-4948 (2001).
Riley et al., "Modulation of TCR-induced transcriptional profiles by ligation of CD28, ICOS, and CTLA-4 receptors," PNAS 99(18):11790-11795 (2002).
Robert et al., "Antibody Cross-Linking of the Thymocyte-Specific Cell Surface Molecule CTX Causes Abnormal Mitosis and Multinucleation of Tumor Cells," Experimental Cell Research, 235:227-237 (1997).
Rottman et al., "The costimulatory molecule ICOS plays an important role in the immunopathogenesis of EAE," Nat Immunol. 2(7):605-11 (2001).
Rutitzky et al., "Disruption of the ICOS-B7RP-1 costimulatory pathway leads to enhanced hepatic immunopathology and increased gamma interferon production by CD4 T cells in murine schistosomiasis," Infection and Immunity 71(7):4040-4044 (2003).
Sakamoto, "Mabs against human, rat, and mouse AILIM/ICOS," Hybridoma and Hybridomics 21(1):86-87 (2002).
Sakamoto et al., "AILIM/ICOS: its expression and functional analysis with monoclonal antibodies," Hybridoma and Hybridomics, 20(5):293-303 (2001).
Salama et al., "Interaction between ICOS-B7RP1 and B7-CD28 costimulatory pathways in alloimmune responses in vivo," American J. of Transplantation 3:390-395 (2003).
Sato et al., "Up-regulation of inducible co-stimulator (ICOS) expression and its regulation of cytokine production in inflammatory bowel disease," Gastroenterology 118(4):A662, (2000).
Schwartz, "Immunology. It takes more than two to tango," Nature 409(6816):31-2 (2001).
Sharpe et al., "The B7-CD28 superfamily," Nature Reviews Immunology 2:116-126 (2002).
Sharpe, "Analysis of lymphocyte costimulation in vivo using transgenic and 'knockout' mice," Current Opinion in Immunology, 7:389-395 (1995).
Sigmund "Are studies in genetically altered mice out of control?" Arterioscler. Thromb. Vasc. Biol., 20:1425-29 (2000).
Skolnick et al., Trendsin Biotech. 2000, 18(1):34-39.
Smith et al., "Inducible constimulatory molecule-B7-related protein 1 interactions are important for the clonal expansion and B cell helper functions of naïve, Th1, and Th2 T cells," J. of Immunol. 170:2310-2315 (2003).
Sperling et al., "ICOS costimulation: It's not just for TH2 cells anymore," Nat Immunol. 2(7):573-4 (2001).
Sperling, "ICOS costimulation: is it the key to selective immunotherapy?," Clin Immunol. 100(3):261-2 (2001).
Sporici et al., "ICOS ligand costimulation is required for T-cell encephalitogenicity," Clin Immunol. 100(3):277-88 (2001).
Sporici et al., "Costimulation of memory T-cells by ICOS: a potential therapeutic target for autoimmunity?" Clin Immunol. 100(3):263-9 (2001).
Stuart et al., "Targeting T cell costimulation in autoimmune disease," Expert Opin. Ther. Targets 6(3):275-289 (2002).
Swallow et al., "B7h, a novel costimulatory homolog of B7.1 and B7.2, is induced by TNFα," Immunity 11:423-432 (1999).
Tafuri et al., "ICOS essential for effective T-helper-cell responses," Nature 409:105-109 (2001).
Tai et al., "A role for CD9 molecules in T cell activation," J. Exp. Med., 184:753-758 (1996).
Tamatani et al., "AILIM/ICOS: a novel lymphocyte adhesion molecule," Intl. Immunol. 12(1):51-55 (2000).
Tamatani et al., "Characteristics of an antibody which induces an ICAM-1-LFA-1-independent adhesion pathway," Proceedings of the Japanese Society for Immunology, vol. 23, Abstract No. H-160 (1993) [Original Japanese and English Language Translation].
Tamura et al., "B7-H1 costimulation preferentially enhances CD28-independent T-helper cell function," Blood 97(6):1809-16 (2001).
Tesciuba et al., "Inducible costimulator regulates Th2-mediated inflammation, but not Th2 differentiation, in a model of allergic airway disease," J Immunol. 167(4):1996-2003 (2001).
Tezuka et al., "Identification and characterization of rat AILIM/ICOS, a novel T-cell costimulatory molecule, related to the CD28/CTLA4 family," Biochem. & Biophysical Res. Comm. 276:335-345 (2000).
Tezuka et al., "Genetic cloning of a lymphocyte surface signal transduction molecule which induces an unknown adhesion phenomenon," Proceedings of the Japanese Society for Immunology, vol. 24, Abstract No. W17-14 (1994) [Original Japanese and English Language Translation].
Tomlinson et al., "The repertoire of human germline VH sequences reveals about fifty groups of VH segments with different hypervariable loops," J. Mol. Biol. 227(3):776-98 (1992).
Totsuka et al., "Ameliorating effect of anti-inducible costimulator monoclonal antibody in a murine model of chronic colitis," Gastroenterology 124:410-421 (2003).
Vermaelen et al., "Accelerated airway dendritic cell maturation, trafficking and elimination in a mouse model of asthma," Am J Respir Cell Mol Biol. 29(3 Pt 1):405-9 (2003).
Villegas et al., "A role for inducible costimulator protein in the CD28-independent mechanism of resistance to *Toxoplasma gondii*," J. of Immunol. 169:937-943 (2002).
Wahl et al., "Renal tubular epithelial expression of the costimulatory molecule B7RP-1 (Inducible Costimulator Ligand)," J. Am. Soc. Nephrol. 13:1517-1526 (2002).
Wall "Transgenic livestock: progress and prospects for the future" Theriogenology 45:57-68 (1996).
Wallin et al., "Enhancement of CD8+ T cell responses by ICOS/B7h costimulation," J Immunol. 167(1):132-9 (2001).
Wang et al., "Costimulation of T cells by B7-H2, a B7-like molecule that binds ICOS," Blood 96(8):2808-2813 (2000).
Wang et al., "Ligand binding sites of inducible costimulator and high avidity mutants with improved function," J. Exp. Med. 195(8):1033-1041 (2002).
Wiendl et al., "Muscle fibres and cultured muscle cells express the B7.1/2-related inducible co-stimulatory molecule, ICOSL: implications for the pathogenesis of inflammatory myopathies," Brain 126:1026-1035 (2003).
Wiley et al., "Evaluation of inducible costimulator/B7-related protein-1 as a therapeutic target in a murine model of allergic airway inflammation," Am. J. Respir. Cell Mol. Biol. 28:722-730 (2003).
Witsch et al., "ICOS and CD28 reversely regulate IL-10 on reactivation of human effector T cells with mature dendritic cells," Eur. J. Immunol. 32:2680-2686 (2002).
Wong et al., "Impaired germinal center formation and recall T cell-dependent immune responses in mice lacking the co-stimulatory ligand B7-H2," Blood 102(4):1381-1388 (2003).
Yoshinaga et al., "Characterization of a new human B7-related protein: B7RP-1 is the ligand to the co-stimulatory protein ICOS," International Immunol. 12(10):1439-1447 (2000).
Yoshinaga et al., "T-cell co-stimulation through B7RP-1 and ICOS," Nature 402:827-832 (1999).

* cited by examiner

REMEDIES FOR INFLAMMATORY BOWEL DISEASES

CROSS REFERENCE TO RELATED APPLICATIONS

This application is a continuation of U.S. application Ser. No. 10/472,743, filed Mar. 4, 2004, which is a national phase filing under 35 U.S.C. §371 of international application number PCT/JP02/01361, filed Feb. 18, 2002, which claims the benefit of priority of Japanese application number 2001-89158, filed Mar. 27, 2001, and Japanese application number 2002-19291, filed Jan. 29, 2002. The disclosures of the prior applications are considered part of (and are incorporated by reference in) the disclosure of this application.

TECHNICAL FIELD

The present invention relates to pharmaceutical compositions comprising a substance having an activity to modulate the biological activity of the "activation inducible lymphocyte immunomodulatory molecule" (AILIM) (also known as "inducible costimulator" (ICOS)), especially the signal transduction mediated by AILIM.

Specifically, the present invention relates to pharmaceutical compositions comprising a substance having an activity to regulate (for example, inhibit) the proliferation of AILIM-expressing cells, cell death (or apoptosis), or immune cytolysis, or to modulate (for example, inhibit) the production of a cytokine (for example, interferon-γ, or interleukin-4) by AILIM-expressing cells.

More specifically, the present invention comprises substances having an activity to U the signal transduction via AILIM, and particularly preferably, substances that induce cell death, apoptosis, or depletion of AILIM-expressing cells. The present invention relates to pharmaceutical compositions for suppressing, treating, or preventing diseases accompanying abnormal immunity of the intestinal tract (for example, inflammatory bowel diseases such as colitis (ulcerative colitis and such) and Crohn's disease, and alimentary allergies).

BACKGROUND ART

Mucous membranes of the gastrointestinal tract are constantly exposed not only to antigens derived from food and enterobacterial flora, but also to various antigens existing in the outside world that are harmful to the living body, such as pathogenic microorganisms. Therefore, the gastrointestinal mucous membranes exhibit a cytotoxic activity in order to compete against such antigens harmful to the living body. While maintaining the ability to secrete antibodies to neutralize toxins, these mucous membranes also have the unique immune mechanism of suppressing excessive immune reactions against antigens such as food and enterobacterial flora (this mechanism is called gastrointestinal mucosal immunity or intestinal immunity). Specifically, normal mucosal immunity is established on the balance between positive immune responses against pathogens and negative immune responses against non-pathogenic antigens. When this balance of immunological homeostatic maintenance collapses, inflammation, allergies, and infections occur, triggering the onset of intestinal diseases generally termed Inflammatory Bowel Diseases (IBD) and alimentary allergies.

The most representative inflammatory bowel diseases are Crohn's disease (CD) and colitis (especially Ulcerative Colitis (UC)). Both are diseases in which the pathogen cannot be specified and chronic and recurrent attacks of abdominal pain and diarrhea occur, causing significant, long-term obstacles to the daily life of child and juvenile patients. Furthermore, since colitis (especially ulcerative colitis) may become a causative for colon cancer, there is an urgent need for elucidating the pathogenesis of colitis and developing effective therapeutic methods.

Although various possibilities such as genetic and environmental factors have been discussed concerning the mechanism of onset for inflammatory bowel diseases, recent studies indicate the strong possibility that abnormal immunity of the intestinal tract (gastrointestinal mucosal immunity) may be the cause. More specifically, an inflammation or allergy occurs in the intestinal mucous membranes due to the induction of an excessive immune response that occurs for some reason against antigens in the intestine that are normally non-pathogenic and have a low immunogenicity, resulting in the onset of an inflammatory bowel disease.

Furthermore, abnormal immunity against foreign pathogens, antigens derived from food, or autoantigens has been suggested to be deeply involved in such inflammations and allergies of the intestine. Furthermore, recent studies have suggested the possibility that abnormal immune responses towards certain indigenous bacteria manifest as chronic inflammatory reactions.

This mechanism of onset of inflammations and allergies of the intestine due to abnormal immunity of the intestinal tract is supported by analyses on the function and differentiation of T cells of patients as well as the cytokine production pattern in lesions or serum. Furthermore, analysis of various recently developed animal models of inflammatory intestinal diseases also reveal that abnormal mucosal immunity causes chronic inflammation in the intestine (Gastroenterology, Vol. 109, p. 1344-1367, 1995).

For example, it is clear that T cells are deeply involved in the onset of chronic enteritis since inflammation of the intestine develops spontaneously in T cell receptor (TCR) α-chain knockout mice (TCRα$^{-/-}$)(Cell, Vol. 75, p. 275-282, 1993; J. Exp. Med., Vol. 183, p. 847-856, 1996). In colitis of these TCRα$^{-/-}$ mice, the production of IFN-γ in the intestine is elevated, and in the initial stage of inflammation, a rise in IL-1α and IL-1β levels is seen (Laboratory Investigation, Vol. 76, p. 385-397, 1997). Furthermore, TCBβ ($\beta^{dim}$) T cells that have a specific Vβ subset and produce IL-4 can be seen in the digestive tract and lymph nodes (Gastroenterology, Vol. 112, p. 1876-1886, 1997). In this model, it is thought that a deficiency of TCRαβ T cells causes an increase in the fraction of abnormal T cells, which then causes abnormal regulation of cytokine production, becoming a mediator of inflammation.

In a model in which CD4$^+$/CD45RB$^{high}$ T cells are introduced to severe combined immunodeficient mice (SCID mice), severe enteritis accompanying hyperplasia of a mucosal layer and infiltration of lymphocytes in the intestine are induced. However, this enteritis does not occur when unfractionated CD4$^+$ T cells are simultaneously introduced (J. Exp. Med., Vol. 178, p. 237-244, 1993; Int. Immunol., Vol. 5, p. 1461-1471, 1993). CD4$^+$ T cells of SCID mice that have developed enteritis produce IFN-γ. On the other hand, since enteritis is suppressed by the administration of antibodies against INF-γ, Th1 type T cells are considered to cause the inflammation (Immunity, Vol. 1, p. 553-562, 1994).

Based on these facts, there seems to be no doubt that CD4$^+$ T cells of the intestine and excessive activation thereof are important factors in inflammatory bowel diseases.

Furthermore, regression of enteritis with the decrease in CD4$^+$ T cells in patients affected by both an inflammatory bowel disease and HIV, also supports the deep involvement of abnormal CD4$^+$ T cells in inflammatory bowel diseases (J.

Clin. Gastroenterology, Vol. 23, p. 24-28, 1996). Based on this finding, there have been attempts to treat inflammatory bowel diseases using an anti-CD4 antibody, and it has been reported that inflammatory lesions are suppressed by the administration of an anti-CD4antibody(Gut, Vol. 40, p. 320-327, 1997).

On the other hand, such abnormal functional regulation of T cells means that the balance of regulatory cytokine production has collapsed.

In fact, enteritis is also reported to develop spontaneously in IL-2knockout mice and IL-10 knockout mice (Cell, Vol. 75, p. 235-261, 1993; Cell, Vol. 75, p. 263-274, 1993). Furthermore, in these models, excess production of IFN-γ is also observed, supporting the fact that an excessive Th1 type T cell reaction has occurred. Overproduction of IFN-γ in these models is consistent with the observation of increased expression of IFN-γ in lesions seen in Crohn's disease. Enteritis can be treated in IL-10 deficient mice by administering IL-10. It has been reported that enteritis can be suppressed by this method in SCID mice to which $CD4^+/CD45RB^{high}$ T cells have been introduced (Immunity, Vol. 1, p. 553-562, 1994).

As mentioned above, the analysis of the mechanism of onset of inflammatory bowel diseases has progressed from the aspect of abnormal gastrointestinal mucosal immunity, suggesting the possibility of treating inflammatory bowel diseases by suppressing increased activation of $CD4^+$ T cells and overproduced cytokines. However, the real pathogenesis of inflammatory bowel diseases has not yet been revealed, and furthermore, an effective therapeutic method has not been provided.

The activation of T cells (acquisition of antigen specificity) is initiated when T cells recognize antigens presented by antigen-presenting cells (APCs) such as macrophages, B cells, or dendritic cells. APCs process the incorporated antigens, and the processed antigens are bound to the major histocompatibility antigen complex (MHC) and presented. T cells receive the first signal for cell activation (acquisition of specificity) as a result of the recognition of the processed antigen presented by APCs through a complex formed between the T cell receptor (TCR) on the T cell membrane surface and the antigen (TCR/CD3 complex).

For sufficient activation of T cells, a second signal called the costimulatory signal is necessary in addition to the first signal. T cells are activated antigen-specifically by receiving this costimulatory signal after receiving the first signal.

For this second signal transduction, the interaction (more specifically, the intercellular adhesion mediated by bonds formed between the following molecules) among CD28 (also known as Tp44, T44, or 9.3 antigen), which is a cell surface molecule expressed mainly in T cells and thymus cells, CD80 (also known as B7-1, B7, BB1, or B7/BB1), which is a cell surface molecule expressed by antigen-presenting cells (macrophages, monocytes, dendritic cells, etc.), and CD86 (also known as B7-2 or B70), which is also a cell surface molecule on antigen-presenting cells, is extremely important.

Furthermore, it has been experimentally revealed that the interaction (specifically, the intercellular adhesion mediated by bonds formed between the following molecules) among Cytolytic T Lymphocyte-associated Antigen 4 (CTLA-4) whose expression is enhanced depending on the second signal, CD80 (B7-1), and CD86 (B7-2) also has an important role in the regulation of T cell activation by this second signal. More specifically, the regulation of T cell activation by this second signal transduction has been revealed to include at least the interaction between CD28 and CD80/CD86, enhancement of the expression of CTLA-4 considered to be dependent on this interaction, and the interaction between CTLA-4 and CD80/CD86.

In addition, recently, similarly to CTLA4 and CD28 described above, a molecule called activation inducible lymphocyte immunomodulatory molecule (AILIM; human, mouse, and rat; Int. Immunol., 12(1), p. 51-55, 2000; also called Inducible co-stimulator (ICOS; human; Nature, 397 (6716), p. 263-266, 1999); J. Immunol., 166(1), p. 1, 2001; J. Immunol., 165(9), p. 5035, 2000; Biochem. Biophys. Res. Commun., 276(1), p. 335, 2000; Immunity, 13(1), p. 95, 2000; J. Exp. Med., 192(1), p. 53, 2000; Eur. J. Immunol., 30(4), p. 1040, 2000) was identified as the third costimulatory transmission molecule that transduces a second signal (co-stimulatory signal) necessary for the activation of lymphocytes such as T cells, and coupled with the signal, regulates the function of activated lymphocytes such as activated T cells.

Furthermore, a novel molecule called B7h, B7RP-1, GL50, or LICOS which is considered to be a ligand interacting with the costimulatory transmission molecule AILIM has been identified (Nature. Vol. 402, No. 6763, pp. 827-832, 1999; Nature Medicine, Vol. 5, No. 12, pp. 1365-1369, 1999; J. Immunology, Vol. 164, pp. 1653-1657, 2000; Curr. Biol., Vol. 10, No. 6, pp. 333-336, 2000).

Exhaustive studies are in progress on the biological functions of these two novel molecules, the functional control of lymphocytes such as T cells through the third costimulatory signal transduction by the molecules.

On the other hand, there has not been even suggestions on the relationship between AILIM (ICOS), which is the third costimulatory transduction molecule considered essential for the activation of T cells such as $CD4^+$ T cells, and the onset of the above-mentioned abnormal immunity of the intestinal mucous membrane and inflammatory bowel diseases (Crohn's disease and colitis (ulcerative colitis and such)) . Neither has there been any suggestion on attempts to treat inflammatory bowel diseases by regulating the function of this AILIM molecule.

DISCLOSURE OF THE INVENTION

Specifically, an objective of the present invention is to provide methods and pharmaceutical agents for suppressing, treating, or preventing diseases accompanying abnormal immunity (abnormal T cell activation, increase of abnormal $CD4^+$ cells) of the intestinal tract such as inflammatory bowel diseases (Crohn' s disease and colitis (ulcerative colitis and such)) by modulating, via medicinal and pharmaceutical methods (for example, pharmaceutical agents such as low molecular weight compounds and antibodies), the biological function of the novel molecule AILIM, which is considered to transduce the second signal essential for the activation of lymphocytes such as T cells (costimulatory signal) and regulate the function of activated lymphocytes such as activated T cells.

A further objective is to use such pharmaceutical agents that modulate the biological function of AILIM (for example, pharmaceutical agents such as low molecular weight compounds and antibodies) to provide methods for enhancing the therapeutic effect of existing pharmaceutical agents widely used for treating inflammatory bowel diseases (adrenocortical hormones, salazosulfapyridine, etc.).

Extensive studies on methods for suppressing the biological function of mammalian AILIM (ICOS), and alimentary allergies and inflammatory bowel diseases in which abnormal immunity of the intestinal tract may be deeply involved (especially Crohn's disease and colitis (ulcerative colitis and such)), led the present inventors to discover that pharmaceutical agents that regulate the function of AILIM significantly suppress inflammatory bowel diseases (especially Crohn's disease and colitis (ulcerative colitis and such)). Thus, the present invention was achieved.

A pharmaceutical composition of the present invention is useful as a pharmaceutical for modulating various reactions in vivo in which the transduction of a costimulatory signal to AILIM-expressing cells mediated by AILIM is involved (for example, proliferation of AILIM-expressing cells, production of cytokine(s) by AILIM-expressing cells, immune cytolysis or cell death, apoptosis, or depletion of AILIM-expressing cells, and the activity to induce antibody-dependent cellular cytotoxicity against AILIM-expressing cells), and/or as a pharmaceutical for preventing the onset and/or progression of various diseases in which the signal transduction mediated by AILIM is involved, and for the treatment or prophylaxis of the diseases.

Specifically, a pharmaceutical composition of the present invention can modulate (suppress or promote) the proliferation of AILIM-expressing cells, apoptosis, cell death, or depletion, or immune cytolysis, or can modulate (inhibit or promote) the production of cytokines (for example, interferon γ, or interleukin 4) by AILIM-expressing cells, and can prevent various disease conditions triggered by various physiological phenomena in which the signal transduction mediated by AILIM is involved, and enables the treatment or prevention of various diseases.

Such an especially preferred embodiment of the pharmaceutical compositions of this invention are pharmaceutical compositions comprising a substance that induces cell death, apoptosis, or depletion of AILIM expressing cells.

Using the pharmaceutical compositions of this invention, diseases that may be caused by an abnormal immunity of the intestinal tract, more specifically, inflammatory bowel diseases (especially Crohn's disease and colitis (ulcerative colitis and such)) and alimentary allergies can be suppressed, prevented, and/or treated.

Furthermore, the pharmaceutical compositions of this invention can enhance the therapeutic effect on inflammatory bowel diseases when used in combination with an existing pharmaceutical agent prescribed to treat such inflammatory bowel diseases.

More specifically, the present invention is as described in the following (1) to (10).

(1) A pharmaceutical composition for suppressing, treating, or preventing a disease that accompanies abnormal immunity of the intestinal tract, wherein the pharmaceutical composition comprises a substance having an activity to modulate signal transduction via AILIM and a pharmaceutically acceptable carrier.

(2) The pharmaceutical composition of (1) wherein said substance has an activity to induce cell death of an AILIM-expressing cell.

(3) The pharmaceutical composition of (1) or (2), wherein said disease is an inflammatory bowel disease.

(4) The pharmaceutical composition of (3), wherein said inflammatory bowel disease is colitis.

(5) The pharmaceutical composition of (3), wherein said inflammatory bowel disease is Crohn's disease.

(6) The pharmaceutical composition of (1) or (2), wherein said disease is an alimentary allergy.

(7) The pharmaceutical composition of any one of (1) to (6), wherein said substance is a proteinaceous substance.

(8) The pharmaceutical composition of (7) wherein said proteinaceous substance is selected from group consisting of:

a) an antibody that binds to AILIM, or a part of said antibody;

b) a polypeptide comprising the whole extracellular region of AILIM, or a part thereof;

c) a fusion polypeptide comprising the whole or a portion of extracellular region of AILIM, and the whole or a portion of constant region of the immunoglobulin heavy chain; and, d) a polypeptide that binds to AILIM. (9) The pharmaceutical composition of any one of (1) to (6), wherein said substance is a non-proteinaceous substance. (10) The pharmaceutical composition of (9) wherein said non-proteinaceous substance is DNA, RNA, or a chemically synthesized compound.

The present inventions are described in detail herein below by defining the terms and the methods for producing the substances used in this invention.

Herein, the term "mammal" means a human, cow, goat, rabbit, mouse, rat, hamster, and guinea pig; preferred is a human, cow, rat, mouse, or hamster, and particularly preferred is a human.

"AILIM" of this invention is an abbreviation for "Activation Inducible Lymphocyte Immunomodulatory Molecule" and denotes a cell surface molecule of a mammal having the structure and function described in previous reports (J. Immunol., 166(1), p. 1, 2001; J. Immunol., 165(9), p. 5035, 2000; Biochem. Biophys. Res. Commun., 276(1), p. 335, 2000; Immunity, 13(1), p. 95,2000; J. Exp. Med., 192(1), p. 53, 2000; Eur. J. Immunol., 30(4), p. 1040, 2000; Int. Immunol., 12(1), p. 51, 2000; Nature, 397(6716), p. 263, 1999; GenBankAccession Number: BAA82129 (human); BAA82128 (rat); BAA82127 (mutant rat); BAA82126 (mouse)).

Especially preferably, the term denotes AILIM derived from a human (for example, International Immunology, Vol. 12, No. 1, p. 51-55, 2000; GenBank Accession Number: BAA82129).

This AILIM is also called ICOS (Nature, Vol. 397, No. 6716, p. 263-266, 1999) or JTT-1 antigen/JTT-2 antigen (Unexamined Published Japanese Patent Application No. (JP-A) Hei 11-29599, International Patent Application No. WO98/38216), and these molecules mutually refer to the same molecule.

In addition, "AILIM" in this invention includes the amino acid sequences of AILIM from each mammal described in previously reported literature, and especially preferably, a polypeptide having substantially the same amino acid sequence as that of human AILIM. Furthermore, human AILIM mutants similar to the previously identified AILIM mutant derived from rat (GenBank Accession Number: BAA82127) are also included in the "AILIM" of this invention.

Herein, the expression "having substantially the same amino acid sequence" means that "AILIM" of the present invention includes polypeptides having an amino acid sequences in which multiple amino acids, preferably 1 to 10 amino acids, particularly preferably 1 to 5 amino acids, have been substituted, deleted, and/or modified, and polypeptides having an amino acid sequences in which multiple amino acids, preferably 1 to 10 amino acids, particularly preferably 1 to 5 amino acids, have been added, as long as the polypeptides have substantially the same biological properties as the polypeptide comprising the amino acid sequence shown in previous reports.

Such substitutions, deletions, or insertions of amino acids can be achieved according to the usual method (Experimental Medicine: SUPPLEMENT, "Handbook of Genetic Engineering" (1992), etc.).

Examples are synthetic oligonucleotide site-directed mutagenesis (gapped duplex method), point mutagenesis by which a point mutation is introduced at random by treatment with nitrite or sulfite, the method by which a deletion mutant is prepared with Bal31 enzyme and so on, cassette mutagenesis, linker scanning method, misincorporation method, mismatch primer method, DNA segment synthesis method, etc.

Synthetic oligonucleotide site-directed mutagenesis (gapped duplex method) can be performed, for example, as follows. The region one wishes to mutagenize is cloned into a M13 phage vector having an amber mutation to prepare a single-stranded phage DNA. After RF I DNA of M13 vector having no amber mutation is linearized by restriction enzyme treatment, the DNA is mixed with the single-stranded phage DNA mentioned above, denatured, and annealed thereby forming a "gapped duplex DNA." A synthetic oligonucleotide into which mutations are introduced is hybridized with the gapped duplex DNA and a closed-circular double-stranded DNA is prepared by reacting with DNA polymerase and DNA ligase. *E. coli* mutS cells, deficient in mismatch repair activity, are transfected with this DNA. *E. coli* cells having no suppressor activity are infected with the grown phages, and only phages having no amber mutations are screened.

The method by which a point mutation is introduced with nitrite utilizes, for example, the principle as mentioned below. If DNA is treated with nitrite, nucleotides are deaminated to change adenine into hypoxanthine, cytosine into uracil, and guanine into xanthine. If deaminated DNA is introduced into cells, "A:T" and "G:C" are replaced with "G:C" and "A:T", respectively, because hypoxanthine, uracil, and xanthine base pair with cytosine, adenine, and thymine, respectively, in DNA replication. Actually, single-stranded DNA fragments treated with nitrite are hybridized with "gapped duplex DNA", and thereafter, mutant strains are separated by manipulating in the same way as synthetic oligonucleotide site-directed mutagenesis (gapped duplex method).

The term "cytokine" as in "production of a cytokine by AILIM-expressing cells" in the present invention means an arbitrary cytokine produced by AILIM-expressing cells (especially, T cells).

Examples of T cells are T cells of the Th1 type or Th2 type, and a cytokine of the present invention specifically means a cytokine produced by T cells of the Th1 type and/or an arbitrary cytokine produced by T cells of the Th2 type.

Cytokines produced by T cells of the Th1type include IFN-γ, IL-2, TNF, IL-3, and cytokines produced by T cells of Th2 type include IL-3, IL-4, IL-5, IL-10, and TNF (Cell, Vol. 30, No. 9, pp. 343-346, 1998).

The expression "substance", "substance having an activity to modulate the signal transduction mediated by AILIM", "substance having an activity to inhibit the proliferation of AILIM-expressing cells, or to inhibit the production of a cytokine by AILIM-expressing cells", or "substance having an activity to induce cell death of AILIM-expressing cells" as used in the present invention means a naturally-occurring substance or an artificially-prepared arbitrary substance.

Particularly preferred embodiment of the "substance" according to this invention is the substance having an activity to induce cell death, apoptosis, or depletion of AILIM-expressing cells.

Herein, the expression "signal transduction mediated by AILIM" means signal transduction through AILIM, leading to a change of any phenotype in the AILIM-expressing cells described above or in the following Examples (a change in cell proliferation, activation of cells, inactivation of cells, apoptosis, and/or the ability to produce an arbitrary cytokine from AILIM-expressing cells). "The substance" can be mainly classified into a "proteinaceous substance" and a "non-proteinaceous substance".

Examples of "proteinaceous substances" are the following polypeptides, antibodies (polyclonal antibodies, monoclonal antibodies, or portions of monoclonal antibodies).

When the substance is an antibody, it is preferably a monoclonal antibody. When the substance is a monoclonal antibody, it includes not only non-human mammal-derived monoclonal antibodies, but also the following recombinant chimeric monoclonal antibodies, recombinant humanized monoclonal antibodies, and human monoclonal antibodies.

When the substance is a polypeptide, it includes the following polypeptides, polypeptide (oligopeptide) fragments, fusion polypeptides, and chemically modified polypeptides. Examples of oligopeptides are peptides comprising 5 to 30 amino acids, preferably 5 to 20 amino acids. A chemical modification can be designed depending on various purposes, for example, to increase half-life in blood in the case of administering in vivo, or to increase tolerance against degradation, or increase absorption in the digestive tract in oral administrations.

Examples of polypeptides are as follows:
(1) A polypeptide containing the whole or a portion of extracellular region of AILIM;
(2) A fusion polypeptide comprising the whole or a portion of extracellular region of AILIM, and the whole or a portion of constant region of the immunoglobulin heavy chain; or
(3) A polypeptide that binds to AILIM.

Examples of "non-proteinaceous substances" are DNA, RNA, and chemically synthesized compounds.

Here, "DNA" means "DNA comprising a partial nucleotide sequence of an antisense DNA designed based on the nucleotide sequence of the DNA (including cDNA and genomic DNA) encoding the above AILIM (preferably human AILIM), or a chemically modified DNA thereof" useful as an antisense DNA pharmaceutical. Specifically, the antisense DNA can inhibit the transcription of DNA encoding AILIM into mRNA, or the translation of the mRNA into a protein by hybridizing to the DNA or RNA encoding AILIM.

The expression "partial nucleotide sequence" as referred to herein refers to a partial nucleotide sequence comprising an arbitrary number of nucleotides in an arbitrary region. A partial nucleotide sequence includes 5 to 100 consecutive nucleotides, preferably 5 to 70 consecutive nucleotides, more preferably 5 to 50 consecutive nucleotides, and even more preferably, 5 to 30 consecutive nucleotides.

When the DNA is used as an antisense DNA pharmaceutical, the DNA sequence can be chemically modified in part in order to extend the half-life (stability) in blood when the DNA is administered to patients, to increase the intracytoplasmic-membrane permeability of the DNA, or to increase the degradation resistance or the absorption of orally administered DNA in the digestive organs. Chemical modifications include, for example, the modification of a phosphate bond, a ribose, a nucleotide, the sugar moiety, and the 3' end and/or the 5' end in the structure of an oligonucleotide DNA.

Modifications of phosphate bonds include, for example, the conversion of one or more bonds to phosphodiester bonds (D-oligo), phosphorothioate bonds, phosphorodithioate bonds (S-oligo), methyl phosphonate (MP-oligo) bonds, phosphoroamidate bonds, non-phosphate bonds or methyl phosphonothioate bonds, or combinations thereof. Modification of a ribose includes, for example, the conversion to 2'-fluororibose or 2'-O-methylribose. Modification of a nucleotide includes, for example, the conversion to 5-propynyluracil or 2-aminoadenine.

Here, the term "RNA" means "RNA comprising a partial nucleotide sequence of an antisense RNA designed based on the nucleotide sequence of the RNA encoding the above AILIM (preferably human AILIM), or a chemically modified RNA thereof" useful as an antisense RNA pharmaceutical. The antisense RNA can inhibit the transcription of the DNA encoding AILIM into mRNA, or the translation of the mRNA into a protein by hybridizing to the DNA or RNA encoding AILIM.

The expression "partial nucleotide sequence" as employed herein, refers to a partial nucleotide sequence comprising an arbitrary number of nucleotides in an arbitrary region. A partial nucleotide sequence includes 5 to 100 consecutive nucleotides, preferably 5 to 70 consecutive nucleotides, more preferably 5 to 50 consecutive nucleotides, and even more preferably 5 to 30 consecutive nucleotides.

The antisense RNA sequence can be chemically modified in part in order to extend the half-life (stability) in blood when the RNA is administered to patients, to increase the intracytoplasmic-membrane permeability of the RNA, or to increase the degradation resistance or the absorption of orally administered RNA in digestive organs. Chemical modifications include modifications such as those that apply to the above antisense DNA.

Examples of "a chemically synthesized compound" are an arbitrary compound excluding the above DNA, RNA and proteinaceous substances, having a molecular weight of about 100 to about 1000, or less, preferably a compound having a molecular weight of about 100 to about 800, and more preferably a molecular weight of about 100 to about 600.

The term "polypeptide" included in the definition of the above "substance" means a portion (a fragment) of a polypeptide chain constituting AILIM (preferably human AILIM), preferably the whole or a portion of an extracellular region of the polypeptide constituting AILIM (1 to 5 amino acids may be optionally added into the N-terminus and/or C-terminus of the region).

AILIM according to the present invention is a transmembrane molecule penetrating the cell membrane, comprising 1 or 2 polypeptide chains.

Herein, a "transmembrane protein" means a protein that is connected to the cell membrane through a hydrophobic peptide region that penetrates the lipid bilayer of the membrane once or several times, and whose structure is, as a whole, composed of three main regions, that is, an extracellular region, a transmembrane region, and a cytoplasmic region, as seen in many receptors or cell surface molecules. Such a transmembrane protein constitutes each receptor or cell surface molecule as a monomer, or as a homodimer, heterodimer or oligomer coupled with one or several chains having the same or different amino acid sequence(s).

Here, an "extracellular region" means the whole or a portion of a partial structure (partial region) of the entire structure of the above-mentioned transmembrane protein where the partial structure exists outside of the membrane. In other words, it means the whole or a portion of the region of the transmembrane protein excluding the region incorporated into the membrane (transmembrane region) and the region existing in the cytoplasm following the transmembrane region (cytoplasmic region). "A fusion polypeptide" included in the above "proteinaceous substance" means a fusion polypeptide comprising the whole or a portion of the extracellular region of a polypeptide constituting AILIM (preferably human AILIM), and "the whole or a portion of the constant region of immunoglobulin heavy chain (Ig, preferably human Ig)". Preferably, the fusion polypeptide is a fusion polypeptide having the extracellular region of AILIM and a portion of the constant region of human IgG heavy chain, and particularly preferably, a fusion polypeptide of the extracellular region of AILIM and a region (Fc) of human IgG heavy chain comprising a hinge region, $C_H2$ domain and $C_H3$ domain. As an IgG, IgG1 is preferable, and as AILIM, human, mouse, or rat AILIM is preferable (preferably human).

The expression "the whole or a portion of the constant region of immunoglobulin (Ig) heavy chain" as used herein means the constant region or the Fc region of human-derived immunoglobulin heavy chain (H chain), or a portion thereof. The immunoglobulin can be any immunoglobulin belonging to any class and any subclass. Specifically, the immunoglobulin includes IgGs (IgG1, IgG2, IgG3, and IgG4), IgM, IgAs (IgA1 and IgA2), IgD, and IgE. Preferably, the immunoglobulin is IgG (IgG1, IgG2, IgG3, or IgG4), or IgM. Examples of particularly preferable immunoglobulins of the present invention are those belonging to human-derived IgGs (IgG1, IgG2, IgG3, or IgG4).

Immunoglobulin has a Y-shaped structural unit in which four chains composed of two homologous light chains (L chains) and two homologous heavy chains (H chains) are connected through disulfide bonds (S-S bonds). The light chain is composed of the light chain variable region ($V_L$) and the light chain constant region ($C_L$). The heavy chain is composed of the heavy chain variable region ($V_H$) and the heavy chain constant region ($C_H$).

The heavy chain constant region is composed of some domains having amino acid sequences unique to each class (IgG, IgM, IgA, IgD, and IgE) and each subclass (IgG1, IgG2, IgG3, and IgG4, IgA1, and IgA2).

The heavy chain of IgGs (IgG1, IgG2, IgG3, and IgG4) is composed of $V_H$, $C_H1$ domain, hinge region, $C_H2$ domain, and $C_H3$ domain in this order from the N-terminus.

Similarly, the heavy chain of IgG1 is composed of $V_H$, $C\gamma_11$ domain, hinge region, $C\gamma_12$ domain, and $C\gamma_13$ domain in this order from the N terminus. The heavy chain of IgG2 is composed of $V_H$, $C\gamma_21$ domain, hinge region, $C\gamma_22$ domain, and $C\gamma_23$ domain in this order from the N-terminus. The heavy chain of IgG3 is composed of $V_H$, $C\gamma_31$ domain, hinge region, $C\gamma_32$ domain, and $C\gamma_33$ domain in this order from the N terminus. The heavy chain of IgG4 is composed of $V_H$, $C\gamma_41$ domain, hinge region, $C\gamma_42$ domain, and $C\gamma_43$ domain in this order from the N-terminus.

The heavy chain of IgA is composed of $V_H$, $C\alpha1$ domain, hinge region, $C\alpha2$ domain, and $C\alpha3$ domain in this order from the N-terminus.

Similarly, the heavy chain of IgA1 is composed of $V_H$, $C\alpha_11$ domain, hinge region, $C\alpha_12$ domain, and $C\alpha_13$ domain in this order from the N-terminus. The heavy chain of IgA2 is composed of $V_H$, $C\alpha_21$ domain, hinge region, $C\alpha_22$ domain, and $C\alpha_23$ domain in this order from the N-terminus.

The heavy chain of IgD is composed of $V_H$, $C\delta1$ domain, hinge region, $C\delta2$ domain, and $C\delta3$ domain in this order from the N-terminus.

The heavy chain of IgM is composed of $V_H$, $C\mu1$ domain, $C\mu2$ domain, $C\mu3$ domain, and $C\mu4$ domain in this order from the N-terminus and has no hinge region as seen in IgG, IgA, and IgD.

The heavy chain of IgE is composed of $V_H$, $C\epsilon1$ domain, $C\epsilon2$ domain, $C\epsilon3$ domain, and $C\epsilon4$ domain in this order from the N-terminus and have no hinge region as seen in IgG, IgA, and IgD.

If, for example, IgG is treated with papain, it is cleaved at a slightly N-terminal side beyond the disulfide bonds existing in the hinge region where the disulfide bonds connect the two heavy chains to generate two homologous Fabs, in which a heavy chain fragment composed of $V_H$ and $C_H1$ is connected to one light chain through a disulfide bond; and one Fc, in which two homologous heavy chain fragments composed of the hinge region, $C_H2$ domain, and $C_H3$ domain are connected through disulfide bonds (See "Immunology Illustrated", original 2nd ed., Nankodo, pp. 65-75 (1992); and "Focus of Newest Medical Science 'Recognition Mechanism of Immune System'", Nankodo, pp. 4-7 (1991); and so on).

Namely, "a portion of the constant region of immunoglobulin heavy chain" mentioned above means a portion of the constant region of an immunoglobulin heavy chain having the structural characteristics as mentioned above, and preferably, is a constant region without the C1 domain, or the Fc region. Specifically, an example thereof is a region composed of the hinge region, C2 domain, and C3 domain from each of IgG, IgA, and IgD, or is a region composed of C2 domain, C3 domain, and C4 domain from each of IgM and IgE. A particularly preferable example thereof is the Fc region of human-derived IgG1.

The fusion polypeptide mentioned above has the advantage of being extremely easy to purify by using affinity column chromatography using the property of protein A, which binds specifically to the immunoglobulin fragment, because the fusion polypeptide of the present invention has a portion of a constant region (for example Fc) of an immunoglobulin such as IgG as mentioned above as a fusion partner. Moreover, since various antibodies against the Fc of various immunoglobulins are available, an immunoassay for the fusion polypeptides can be easily performed with antibodies against the Fc.

"A polypeptide that binds to AILIM" is encompassed in "a polypeptide" included in the definition of the above "substance".

A specific example of "a polypeptide that binds to AILIM" is the whole or a portion of a polypeptide constituting known molecule called B7h, B7RP-1, GL50, or LICOS which is a ligand interacting with AILIM (Nature, Vol. 402, No. 6763, pp. 827-832, 1999; Nature Medicine, Vol. 5, No. 12, pp. 1365-1369, 1999; J. Immunology, Vol. 164, pp. 1653-1657, 2000; Curr. Biol., Vol. 10, No 6, pp. 333-336, 2000).

Preferably, the polypeptide is a polypeptide comprising the whole or a portion of an extracellular region of the above ligand (B7h, B7RP-1, GL50, LICOS), or a fusion polypeptide comprising the polypeptide, and the whole or a portion of the constant region of immunoglobulin heavy chain (preferably human immunoglobulin). Here, the expressions "extracellular region" and "constant region of immunoglobulin heavy chain" have the same meanings as mentioned above.

The polypeptides, portions of the polypeptide (fragment), and fusion polypeptides mentioned above can be produced not only by recombinant DNA technology as mentioned below, but also by a method well known in the art such as a chemical synthetic method or a cell culture method, or a modified method thereof.

The "antibody" of the present invention can be a polyclonal antibody (antiserum) or a monoclonal antibody against mammalian AILIM (particularly preferably human AILIM) defined above, and preferably a monoclonal antibody.

Specifically, the antibody is an antibody having an activity to inhibit proliferation of AILIM-expressing cells by binding to AILIM, or to inhibit production of interferon-γ or interleukin-4 by AILIM-expressing cells through binding to AILIM.

The antibodies of the present invention can be natural antibodies obtained by immunizing mammals such as mice, rats, hamsters, guinea pigs, and rabbits with an antigen such as cells (natural cells, cell lines, tumor cells, etc.) expressing AILIM of the present invention, transformants prepared using recombinant DNA technology so as to overexpress AILIM on the surface thereof, polypeptides constituting AILIM, or the above-mentioned fusion polypeptides comprising the AILIM polypeptide or the extracellular region of AILIM. The antibodies of the present invention also include chimeric antibodies and humanized antibodies (CDR-grafted antibodies) that can be produced by recombinant DNA technology, and human antibodies that can be produced using human antibody-producing transgenic animals.

Monoclonal antibodies include those having any one isotype of IgG, IgM, IgA, IgD, or IgE. IgG or IgM is preferable.

A polyclonal antibody (antisera) or monoclonal antibody can be produced by known methods. Namely, a mammal, preferably, a mouse, rat, hamster, guinea pig, rabbit, cat, dog, pig, goat, horse, or cow, or more preferably, a mouse, rat, hamster, guinea pig, or rabbit is immunized, for example, with an antigen mentioned above with Freund's adjuvant, if necessary.

A polyclonal antibody can be obtained from the serum obtained from the animal so immunized. In addition, monoclonal antibodies are produced as follows. Hybridomas are prepared from the antibody-producing cells obtained from the animal so immunized and myeloma cells that are not capable of producing autoantibodies. The hybridomas are cloned, and clones producing the monoclonal antibodies showing a specific affinity to the antigen used for immunizing the mammal are screened.

Specifically, a monoclonal antibody can be produced as follows. Immunizations are performed by injecting or implanting once or several times an antigen mentioned above as an immunogen, if necessary, with Freund's adjuvant, subcutaneously, intramuscularly, intravenously, through the footpad, or intraperitoneally into a non-human mammal, specifically a mouse, rat, hamster, guinea pig, or rabbit, preferably a mouse, rat, or hamster (including a transgenic animal generated so as to produce antibodies derived from another animal such as a transgenic mouse producing human antibody mentioned below). Usually, immunizations are performed once to four times every one to fourteen days after the first immunization. Antibody-producing cells are obtained from the mammal so immunized in about one to five days after the last immunization. The frequency and interval of immunizations can be appropriately arranged depending on, for example, the property of the immunogen used.

Hybridomas that secrete a monoclonal antibody can be prepared by the method of Köhler and Milstein (Nature, Vol. 256, pp. 495-497 (1975)), or by a modified method thereof. Namely, hybridomas are prepared by fusing antibody-producing cells contained in a spleen, lymph node, bone marrow, or tonsil obtained from a non-human mammal immunized as mentioned above, preferably a spleen, with myelomas without an autoantibody-producing ability, which are derived from, preferably, a mammal such as a mouse, rat, guinea pig, hamster, rabbit, or human, or more preferably, a mouse, rat, or human.

For example, a mouse-derived myeloma P3/X63-AG8.653 (653), P3/NSI/1-Ag4-1 (NS-1), P3/X63-Ag8.U1 (P3U1), SP2/0-Ag14 (Sp2/0, Sp2), PAI, F0, NSO, or BW5147, rat-derived myeloma 210RCY3-Ag.2.3., or human-derived myeloma U-266AR1, GM1500-6TG-A1-2, UC729-6, CEM-AGR, D1R11, or CEM-T15 can be used as a myeloma for cell fusion.

Hybridomas producing monoclonal antibodies can be screened by cultivating hybridomas, for example, in microtiter plates and by measuring the reactivity of the culture supernatant in wells in which hybridoma growth is observed, to the immunogen used for the immunization mentioned above, for example, by an enzyme immunoassay such as RIA and ELISA.

Monoclonal antibodies can be produced from hybridomas by cultivating the hybridomas in vitro or in vivo such as in the ascites fluid of a mouse, rat, guinea pig, hamster, or rabbit, preferably a mouse or rat, more preferably mouse, and isolating the antibodies from the resulting culture supernatant or ascites fluid of a mammal.

Cultivating hybridomas in vitro can be performed depending on, e.g., the property of cells to be cultured, the object of the study, and the various conditions of the culture method, by using known nutrient media or any nutrient media derived from known basal media for growing, maintaining, and storing the hybridomas to produce monoclonal antibodies in the culture supernatant.

Examples of basal media are low calcium concentration media such as Ham'F12 medium, MCDB153 medium, or low calcium concentration MEM medium, and high calcium concentration media such as MCDB104 medium, MEM medium, D-MEM medium, RPMI1640 medium, ASF104 medium, or RD medium. The basal media can contain, for example, sera, hormones, cytokines, and/or various inorganic or organic substances depending on the objective.

Monoclonal antibodies can be isolated and purified from the culture supernatant or ascites fluid mentioned above by saturated ammonium sulfate precipitation, euglobulin precipitation method, caproic acid method, caprylic acid method, ion exchange chromatography (DEAE or DE52), and affinity chromatography using an anti-immunoglobulin column or a protein A column.

A "recombinant chimeric monoclonal antibody" is a monoclonal antibody prepared by genetic engineering, and specifically means a chimeric antibody such as a mouse/human chimeric monoclonal antibody whose variable regions are derived from an immunoglobulin of a non-human mammal (mouse, rat, hamster, etc.) and whose constant regions are derived from human immunoglobulin.

A constant region derived from human immunoglobulin has an amino acid sequence unique to each isotype such as IgG (IgG1, IgG2, IgG3, IgG4), IgM, IgA, IgD, and IgE. The constant region of the recombinant chimeric monoclonal antibody can be that of human immunoglobulin belonging to any isotype. Preferably, it is a constant region of human IgG.

A chimeric monoclonal antibody can be produced, for example, as follows. Needless to say, the production method is not limited thereto.

A mouse/human chimeric monoclonal antibody can be prepared, referring to Experimental Medicine: SUPPLEMENT, Vol. 1.6, No. 10 (1988); and Examined Published Japanese Patent Application No. (JP-B) Hei 3-73280. Namely, it can be prepared by operably inserting the $C_H$ gene (C gene encoding the constant region of H chain) obtained from a DNA encoding human immunoglobulin downstream of active $V_H$ genes (rearranged VDJ gene encoding the variable region of H chain) obtained from a DNA encoding a mouse monoclonal antibody isolated from hybridoma producing the mouse monoclonal antibody, and the $C_L$ gene (C gene encoding the constant region of L chain) obtained from a DNA encoding human immunoglobulin downstream of active $V_L$ genes (rearranged VJ gene encoding the variable region of L chain) obtained from a DNA encoding a mouse monoclonal antibody isolated from hybridoma, into the same vector or a different vector in an expressible manner, followed by transforming host cells with the expression vector, and then by cultivating the transformants.

Specifically, DNAs are first extracted from mouse monoclonal antibody-producing hybridomas by the usual method, digested with appropriate restriction enzymes (for example, EcoRI and HindIII), electrophoresed (using, for example, 0.7% agarose gel), and analyzed by Southern blotting. After an electrophoresed gel is stained, for example with ethidium bromide, and photographed, the gel is given marker positions, washed twice with water, and soaked in 0.25 M HCl for 15 minutes. Then, the gel is soaked in a 0.4 N NaOH solution for 10 minutes with gentle stirring. The DNAs are transferred to a filter for 4 hours by the usual method. The filter is recovered and washed twice with 2×SSC. After the filter is sufficiently dried, it is baked at 75° C. for 3 hours. After baking, the filter is treated with 0.1×SSC/0.1% SDS at 65° C. for 30 minutes. Then, it is soaked in 3×SSC/0.1% SDS. The filter obtained is treated with a prehybridization solution in a plastic bag at 65° C. for 3 to 4 hours.

Next, $^{32}$P-labeled probe DNA and a hybridization solution are added to the bag and reacted at 65° C. about 12 hours. After hybridization, the filter is washed under an appropriate salt concentration, reaction temperature, and time (for example, 2×SSC/0.1% SDS, room temperature, 10 minutes). The filter is put into a plastic bag with a small volume of 2×SSC and subjected to autoradiography after the bag is sealed.

Rearranged VDJ gene and VJ gene encoding H chain and L chain of a mouse monoclonal antibody are identified by Southern blotting mentioned above. The region comprising the identified DNA fragment is fractioned by sucrose density gradient centrifugation and inserted into a phage vector (for example, Charon 4A, Charon 28, λEMBL3, and λEMBL4). *E. coli* (for example LE392 and NM539) is transformed with the phage vector to generate a genomic library. The genomic library is screened by a plaque hybridization technique such as the Benton-Davis method (Science, Vol. 196, pp. 180-182 (1977)) using appropriate probes (H chain J gene, L chain (K) J gene, etc.) to obtain positive clones comprising rearranged VDJ gene or VJ gene. By making a restriction map and determining the nucleotide sequence of the clones obtained, it is confirmed whether genes comprising the desired, rearranged $V_H$ (VDJ) gene or $V_L$ (VJ) gene have been obtained.

Separately, human $C_H$ gene and human $C_L$ gene used for chimerization are isolated. For example, when a chimeric antibody with human IgG1 is produced, Cγ1 gene is isolated as a $C_H$ gene, and Cκ gene as a $C_L$ gene. These genes can be isolated from a human genomic library with mouse Cγ1 gene and mouse Cκ gene, corresponding to human Cγ1 gene and human Cκ gene, respectively, as probes, taking advantage of the high homology between the nucleotide sequences of the mouse immunoglobulin gene and the human immunoglobulin gene.

Specifically, DNA fragments comprising human Cκ gene and an enhancer region are isolated from human λ Charon 4A HaeIII-AluI genomic library (Cell, Vol. 15, pp. 1157-1174 (1978)), for example, using a 3 kb HindIII-BamHI fragment of clone Ig146 (Proc. Natl. Acad. Sci. USA, Vol. 75, pp. 4709-4713 (1978)) and a 6.8 kb EcoRI fragment of clone MEP10 (Proc. Natl.Acad. Sci. USA, Vol. 78, pp. 474-478 (1981)) as probes. In addition, for example, after human fetal hepatocyte DNA is digested with HindIII and fractioned by agarose gel electrophoresis, a 5.9 kb fragment is inserted into λ788 and then human Cγ1 gene is isolated with the probes mentioned above.

Using mouse $V_H$ gene, mouse $V_L$ gene, human $C_H$ gene, and human $C_L$ gene so obtained, and taking the promoter region and enhancer region into consideration, human $C_H$ gene is inserted downstream mouse $V_H$ gene and human $C_L$ gene is inserted downstream mouse $V_L$ gene into an expression vector such as pSV2gpt or pSV2neo with appropriate restriction enzymes and DNA ligase by the usual method. In this case, chimeric genes of mouse $V_H$ gene/human $C_H$ gene and mouse $V_L$ gene/human $C_L$ gene can be respectively inserted into the same expression vector or into different expression vectors.

Chimeric gene-inserted expression vector(s) thus prepared are introduced into myelomas that do not produce antibodies, for example, P3X63·Ag8·653 cells or SP210 cells by the protoplast fusion method, DEAE-dextran method, calcium phosphate method, or electroporation method. The transformants are screened by cultivating in media containing a drug corresponding to the drug resistance gene inserted into the expression vector and, then, cells producing desired chimeric monoclonal antibodies are obtained.

Desired chimeric monoclonal antibodies are obtained from the culture supernatant of antibody-producing cells thus screened.

The "humanized monoclonal antibody (CDR-grafted antibody)" of the present invention is a monoclonal antibody prepared by genetic engineering and specifically means a humanized monoclonal antibody wherein a portion or the whole of the complementarity-determining regions of the hypervariable region are derived from the complementarity-determining regions of the hypervariable region from a monoclonal antibody of an non-human mammal (mouse, rat, hamster, etc.), the framework regions of the variable region are derived from the framework regions of the variable region from human immunoglobulin, and the constant region is derived from a constant region from human-derived immunoglobulin.

The complementarity-determining regions of the hypervariable region exists in the hypervariable region in the variable region of an antibody and means three regions which directly and complementary binds to an antigen (complementarity-determining residues, CDR1, CDR2, and CDR3). The framework regions of the variable region mean four comparatively conserved regions lying upstream, downstream, or between the three complementarity-determining regions (framework region, FR1, FR2, FR3, and FR4).

In other words, a humanized monoclonal antibody means that in which all the regions except a portion or the whole of the complementarity-determining regions of the hypervariable region of a non-human mammal-derived monoclonal antibody have been replaced with their corresponding regions derived from a human immunoglobulin.

The constant region derived from human immunoglobulin has an amino acid sequence unique to each isotype such as IgG (IgG1, IgG2, IgG3, IgG4), IgM, IgA, IgD, and IgE. The constant region of a humanized monoclonal antibody in the present invention can be that from human immunoglobulin belonging to any isotype. Preferably, it is a constant region of human IgG. The framework regions of the constant region derived from human immunoglobulin are not particularly limited.

A humanized monoclonal antibody can be produced, for example, as follows. Needless to say, the production method is not limited thereto.

For example, a recombinant humanized monoclonal antibody derived from mouse monoclonal antibody can be prepared by genetic engineering, referring to Published Japanese Translation of International Publication (JP-WA) No. Hei 4-506458 and JP-A Sho 62-296890. Namely, at least one mouse H chain CDR gene and at least one mouse L chain CDR gene corresponding to the mouse H chain CDR gene are isolated from hybridomas producing mouse monoclonal antibody, and human H chain gene encoding the whole regions except human H chain CDR corresponding to mouse H chain CDR mentioned above and human L chain gene encoding the whole region except human L chain CDR corresponding to mouse L chain CDR mentioned above are isolated from human immunoglobulin genes.

The mouse H chain CDR gene(s) and the human H chain gene(s) so isolated are operably inserted into an appropriate vector so that they can be expressed. Similarly, the mouse L chain CDR gene(s) and the human L chain gene(s) are operably inserted into another appropriate vector so that they can be expressed. Alternatively, the mouse H chain CDR gene(s)/human H chain gene(s) and mouse L chain CDR gene(s)/human L chain gene(s) can be operably inserted into the same expression vector in an expressible manner. Host cells are transformed with the expression vector thus prepared to obtain transformants producing humanized monoclonal antibody. By cultivating the transformants, a desired humanized monoclonal antibody is obtained from the culture supernatant.

The "human monoclonal antibody" is an immunoglobulin in which the entire regions comprising the variable and constant region of H chain, and the variable and constant region of L chain constituting the immunoglobulin are derived from genes encoding human immunoglobulin.

The human antibody (preferably human monoclonal antibody) can be produced by well known methods, for example, in the same way as the production method of polyclonal or monoclonal antibodies mentioned above by immunizing, with an antigen, a transgenic animal prepared by integrating at least a human immunoglobulin gene into the gene locus of a non-human mammal such as a mouse.

For example, a transgenic mouse producing human antibodies is prepared by the methods described in Nature Genetics, Vol. 7, pp. 13-21(1994); Nature Genetics, Vol. 15, pp. 146-156 (1997); JP-WA Hei 4-504365; JP-WA Hei 7-509137; Nikkei Science, No. 6, pp. 40-50 (1995); WO94/25585; Nature, Vol. 368, pp. 856-859 (1994); and JP-WA No. Hei 6-500233.

In addition, a recently developed technique for producing a human-derived protein from the milk of a transgenic cow or pig can also be applied (Nikkei Science, pp. 78-84 (April, 1997)).

The expression "portion of an antibody" as used in the present invention means a partial region of a monoclonal antibody as mentioned above. It specifically means $F(ab')_2$, Fab', Fab, Fv (variable fragment of antibody), sFv, dsFv (disulfide stabilized Fv), or dAb (single domain antibody) (Exp. Opin. Ther. Patents, Vol. 6, No. 5, pp. 441-456 (1996)).

"$F(ab')_2$" and "Fab'" can be produced by treating immunoglobulin (monoclonal antibody) with a protease such as pepsin and papain, and means an antibody fragment generated by digesting the immunoglobulin near the disulfide bonds in the hinge regions existing between each of the two H chains. For example, papain cleaves IgG upstream of the disulfide bonds in the hinge regions existing between each of the two H chains to generate two homologous antibody fragments in which an L chain composed of $V_L$ (L chain variable region) and $C_L$ (L chain constant region), and an H chain fragment composed of $V_H$ (H chain variable region) and $C_H\gamma1$ ($\gamma1$ region in the constant region of H chain) are connected at their C terminal regions through a disulfide bond. Each of such two homologous antibody fragments is called Fab'. Pepsin also cleaves IgG downstream of the disulfide bonds in the hinge regions existing between each of the two H chains to generate an antibody fragment slightly larger than the fragment in which the two above-mentioned Fab's are connected at the hinge region. This antibody fragment is called F(ab')$_2$. The expressions, "immunity of the intestinal tract", "gastrointestinal immunity", and "mucosal immunity" of this invention are used to express almost the same meaning.

A preferred example of a "disease accompanying abnormal immunity of the intestinal tract" of this invention may be an inflammatory bowel disease or an alimentary allergy.

A representative example of an "inflammatory bowel disease" of this invention is colitis (especially Ulcerative Colitis (UC)) or Crohn's disease (CD), each having, for example, the following characteristics.

Inflammatory bowel diseases (IBD) can be classified into colitis (especially ulcerative colitis) and Crohn's disease. These diseases frequently develop in juveniles and are considered to be intractable chronic inflammatory diseases that repeat remission and recurrence and, having unknown causes.

Crohn's disease is a disease in which chronic granulomatous inflammations and ulcers occur in the entire digestive tract from the esophagus to the anus, mainly in the small intestine and large intestine, showing symptoms such as abdominal pain, diarrhea, fever, abnormalities of the anus including hemorrhoids, and/or a decrease in body weight. Histologically, a heavy infiltration of lymphocytes and non-caseous epithelioid granuloma are observed, suggesting an abnormal reaction of T cells and antigen-presenting cells.

Colitis (especially ulcerative colitis) is a chronic inflammation that develops locally in the large intestine. It mainly affects the mucous membrane and forms sores and ulcerations. Histologically, a significant infiltration of lymphocytes, plasma cells, macrophage, and mast cells are observed in the mucous membrane and lamina propria mucosae, and cryptic ulcers accompanying an infiltration of neutrophils and a disappearance of goblet cells occur.

The existing pharmaceutical agents used for the treatment of inflammatory bowel diseases of this invention refer to one or more arbitrary pharmaceutical agents clinically prescribed to treat colitis (ulcerative colitis and such) and Crohn's disease, and examples are adrenocortical hormones, and salazosulfapyridine.

The expression "pharmaceutically acceptable carrier" of this invention includes an excipient, a diluent, a filler, a decomposing agent, a stabilizer, a preservative, a buffer, an emulsifier, an aromatic agent, a colorant, a sweetener, a viscosity-increasing agent, a flavor, a solubility-increasing agent, or some other additive. Using one or more of such carriers, a pharmaceutical composition can be formulated into tablets, pills, powders, granules, injections, solutions, capsules, troches, elixirs, suspensions, emulsions, syrups, etc.

The pharmaceutical composition can be administered orally or parenterally. Other forms for parenteral administration include a solution for external application, suppository for rectal administration, and pessary, prescribed by the usual method, which comprises one or more active ingredients.

The dosage can vary depending on the age, sex, weight, and symptoms of a patient, effect of treatment, administration route, period of treatment, the kind of active ingredient (the "substance" according to the present invention, mentioned above) contained in the pharmaceutical composition, etc. Usually, the pharmaceutical composition can be administered to an adult in a dose of 10 µg to 1000 mg (or 10 µg to 500 mg) per one administration. Depending on various conditions, a dosage less than that mentioned above may be sufficient in some cases and a dosage more than that mentioned above may be necessary in others.

In the case of an injection, it can be produced by dissolving or suspending an antibody in a non-toxic, pharmaceutically acceptable carrier such as physiological saline or commercially available distilled water for injection adjusting the concentration in the range of 0.1 µg antibody/ml carrier to 10 mg antibody/ml carrier. The injection thus produced can be administered to a human patient in need of treatment in the dose range of 1 µg to 100 mg/kg body weight, preferably in the range of 50 µg to 50 mg/kg body weight, one or more times a day. Examples of administration routes are medically appropriate administration routes such as intravenous injection, subcutaneous injection, intradermal injection, intramuscular injection, intraperitoneal injection, or such, preferably intravenous injection.

The injection can also be prepared into a non-aqueous diluent (for example, propylene glycol, polyethylene glycol, vegetable oil such as olive oil, and alcohol such as ethanol), suspension, or emulsion.

The injection can be sterilized by filtration with a bacteria-filtering filter, by mixing a bacteriocide, or by irradiation. The injection can be produced in such a manner that it is prepared at the time of use. Namely, it is freeze-dried to be a sterile solid composition that can be dissolved in sterile distilled water for injection or another solvent before use.

Using the pharmaceutical compositions of this invention, diseases that may be caused by abnormal immunity of the intestinal tract, more specifically, inflammatory bowel diseases (especially Crohn's disease and colitis (especially ulcerative colitis)) and alimentary allergies can be suppressed, prevented, and/or treated.

Furthermore, by using the pharmaceutical composition of this invention, it is possible to enhance the therapeutic effect of existing pharmaceutical agents that are prescribed for the treatment of such inflammatory diseases.

● : negative control antibody (n=20)

○ : anti-AILIM/ICOS antibody (n=20)

□ : anti-B7RP-1 antibody (n=7)

■ : administration of negative control antibody to a BALB/c scid/scid mouse to which CD4$^+$CD45RB$^{low}$ T cells have been introduced instead of CD4$^+$CD45RB$^{high}$ T cells (n=7)

Figure 4:
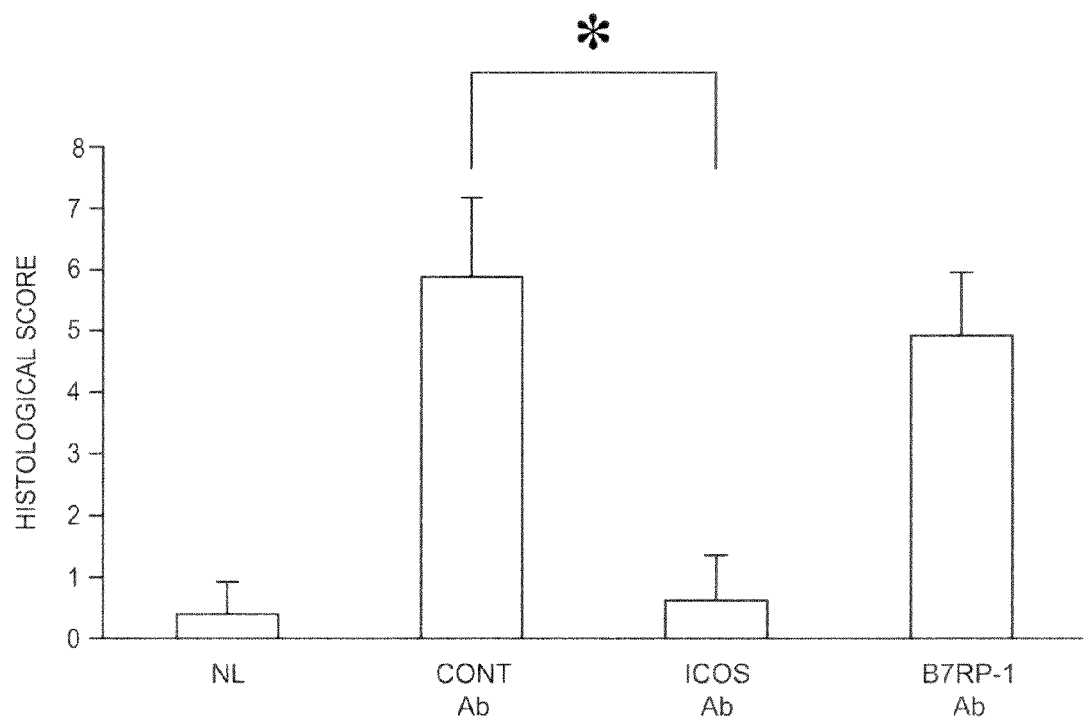

FIG. 4 shows the degree of severity of colitis expressed as histological scores.

Figure 5:
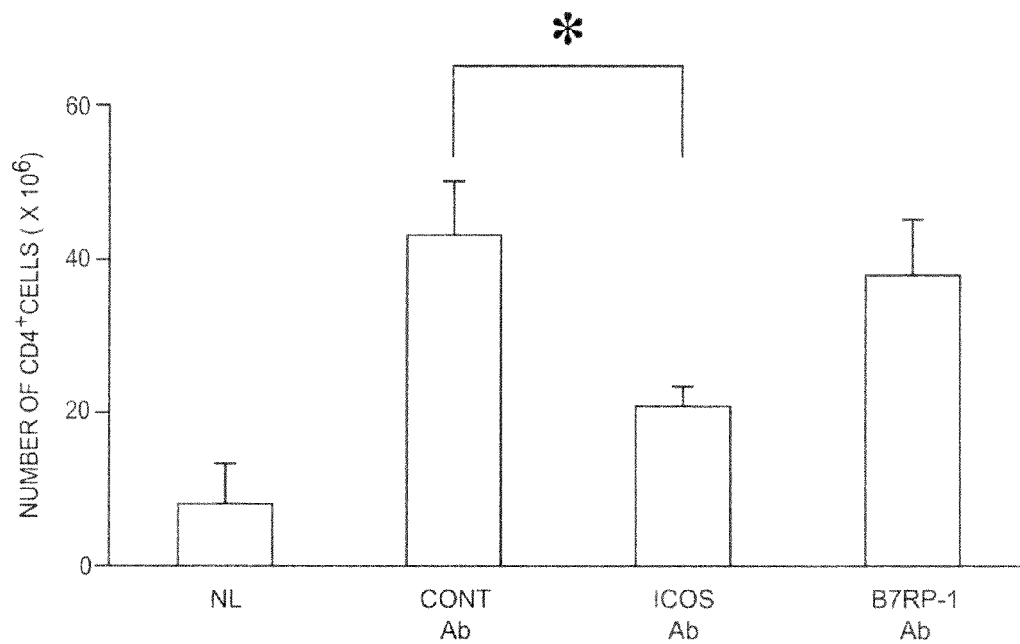

FIG. 5 shows the number of CD4$^+$ cells that infiltrated into the colonic mucosal layer (lamina propria).

Figure 6:
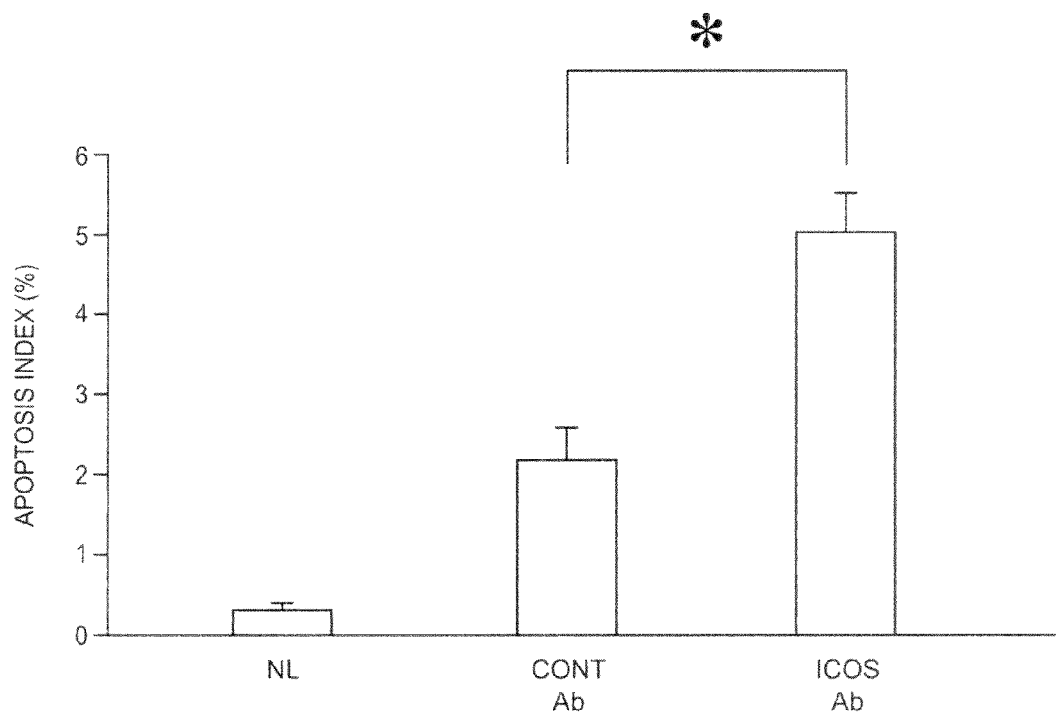

FIG. 6 shows the degree of apoptosis of cells in colon tissues.

Figure 7:
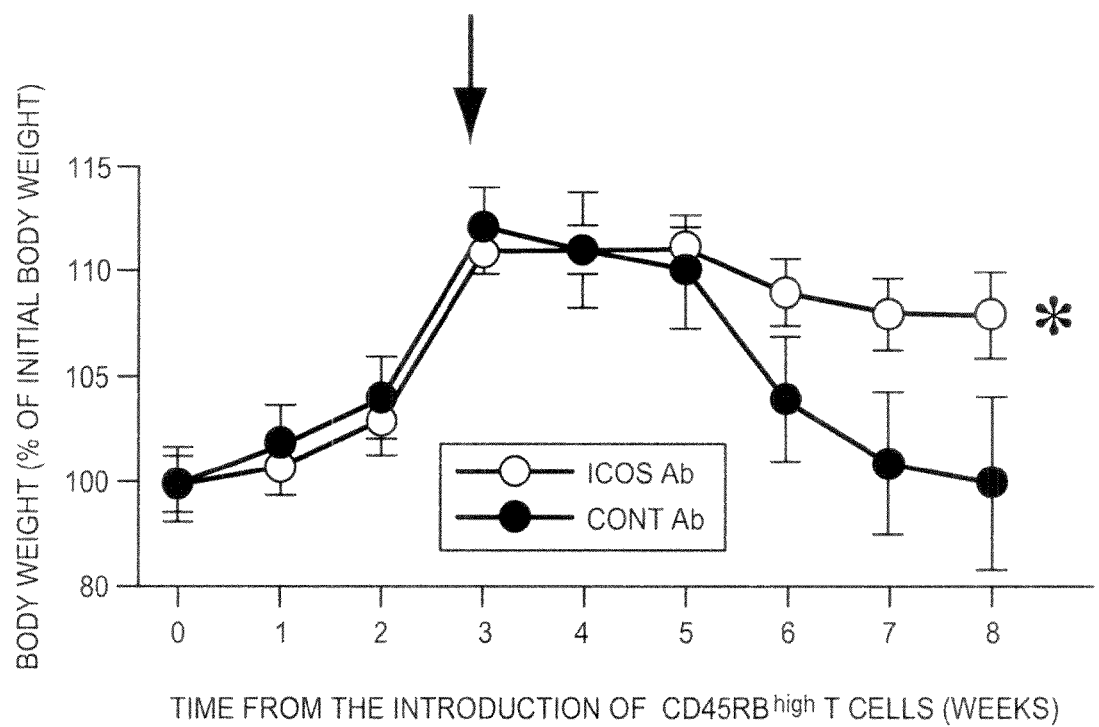
Figure 8:
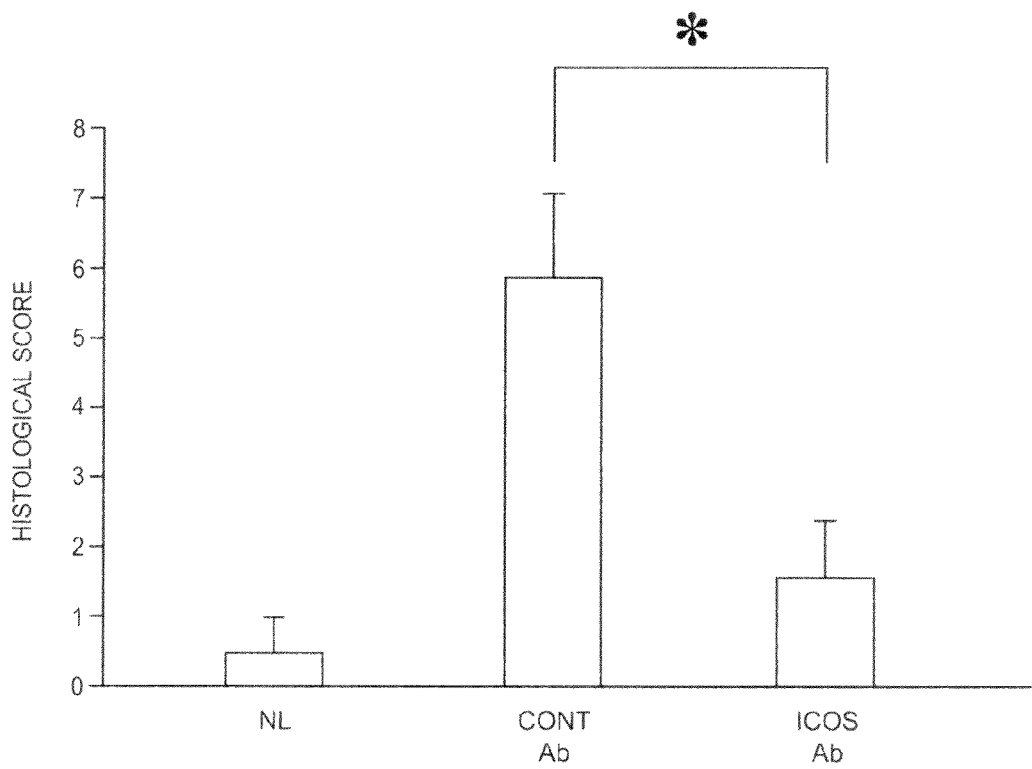

FIG. 7 shows the therapeutic effect of the administration of the anti-AILIM antibody (administration after disease progression) on the inflammatory bowel disease, as determined using weight loss, which is a characteristic of colitis, as an index ● : negative control antibody
□ : anti-AILIM/ICOS antibody FIG. 8 shows the degree of severity of colitis expressed as histological scores.

Figure 9:
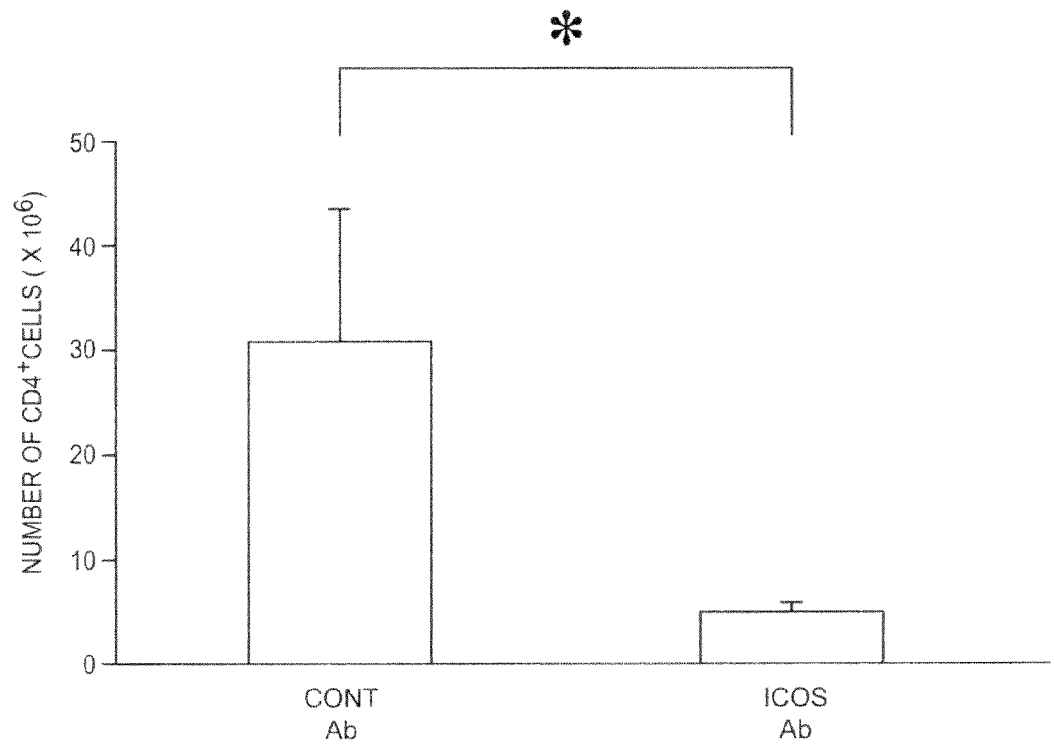

FIG. 9 shows the number of CD4$^+$ cells that infiltrated into the colonic mucosal layer (lamina propria).

Figure 10:
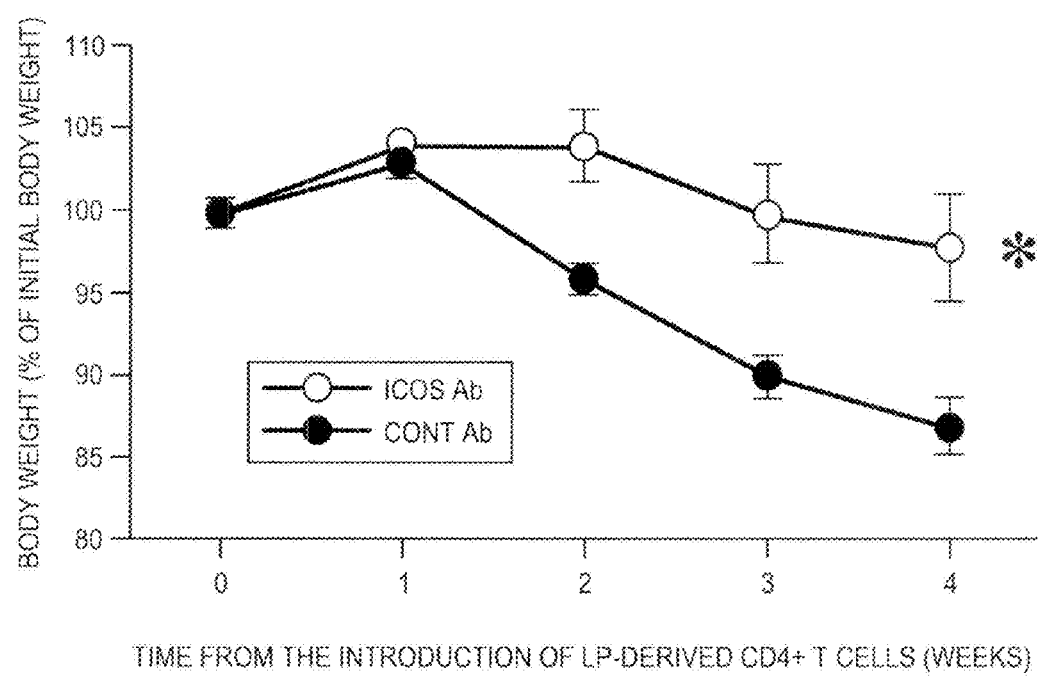

FIG. 10 shows the suppressive effect of the continuously administered anti-AILIM antibody on the onset of the inflammatory bowel disease, as determined using weight loss, which is a characteristic of colitis, as an index.

● : negative control antibody (n=7)
□ : anti-AILIM/ICOS antibody (n=7)

Figure 11:
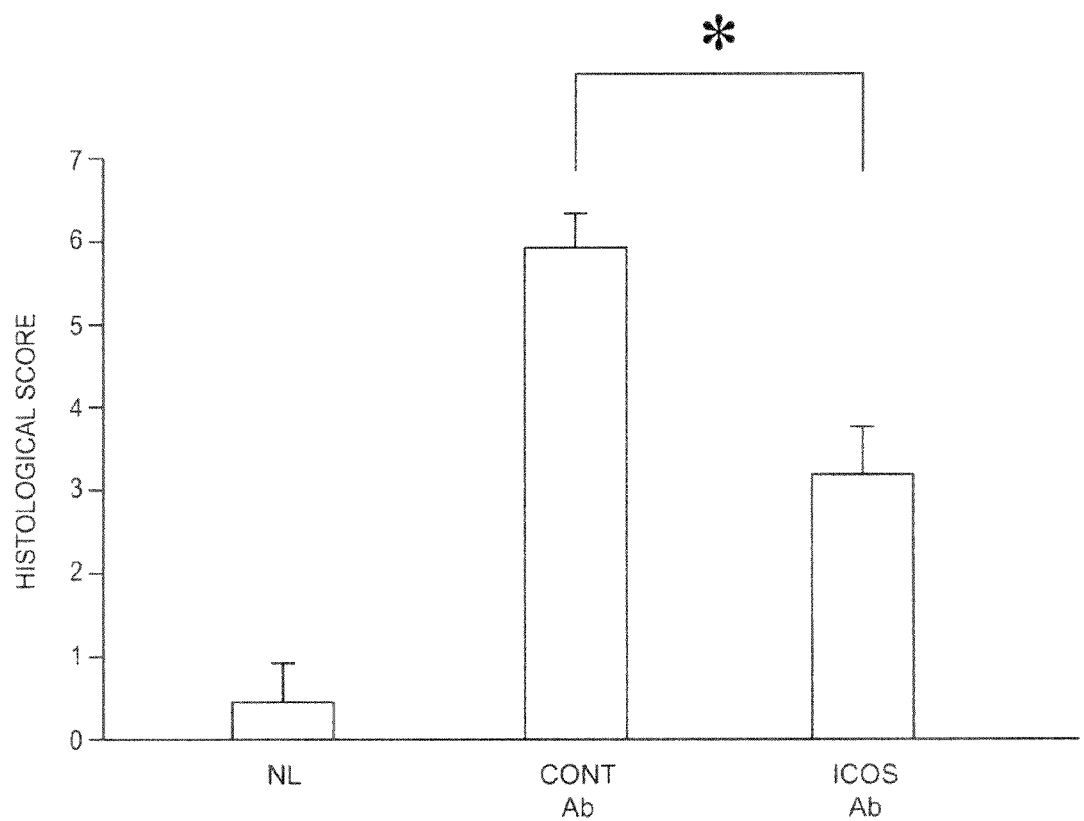

FIG. 11 shows the degree of severity of colitis expressed as histological scores.

Figure 12:
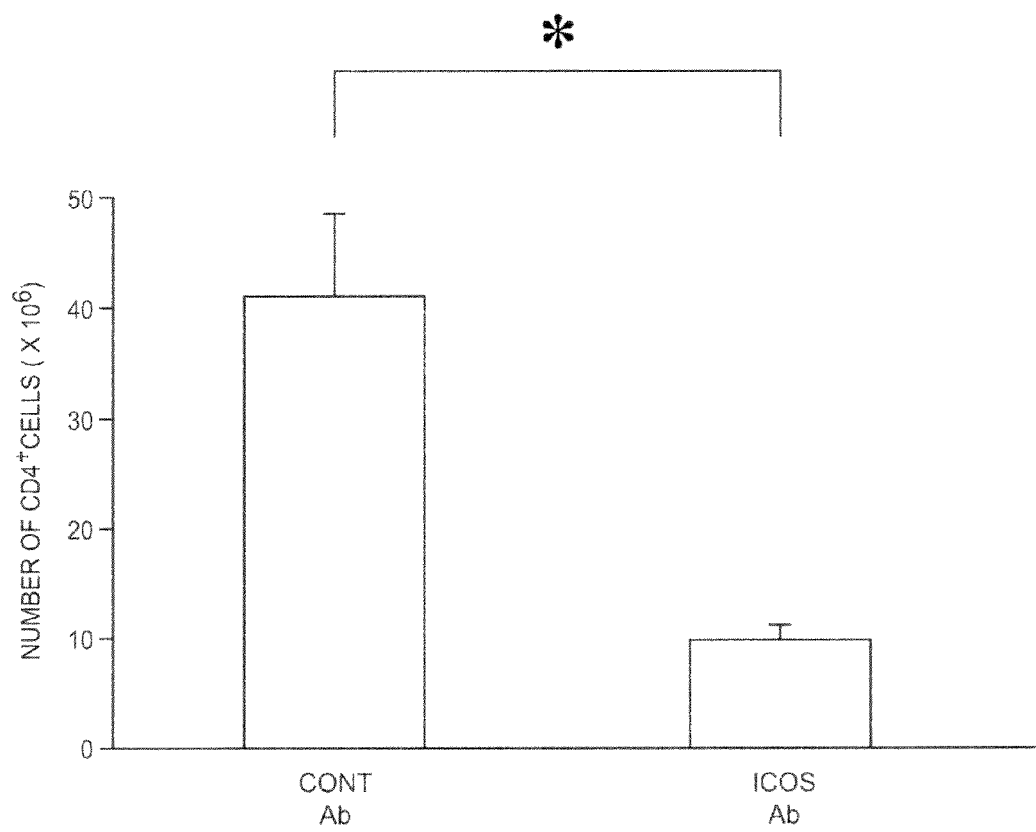

FIG. 12 shows the number of CD4$^+$ cells that infiltrated into the colonic mucosal layer (lamina propria).

BEST MODE FOR CARRYING OUT THE INVENTION

Hereinafter, the present invention is specifically illustrated with reference to Examples, but it is not to be construed as being limited thereto.

Example 1

The Therapeutic Effect on Colitis in a Mouse Colitis Model <Trial 1>

<1-1> Animals

BALB/c scid/scid mice, severely immunodeficient mice (6-8 weeks old females; CLEA Japan), and normal BALB/c mice (6-8 weeks old males; CLEA Japan) were used.

<1-2> Preparation of an Anti-mouse AILIM Monoclonal Antibody

The preparation was done as follows.

Using the cDNA encoding the full length amino acid sequence of the previously reported mouse AILIM (Int. Immunol., Vol. 12, No. 1, p. 51-55, 2000), a transformed cell expressing mouse AILIM was prepared according to standard methods using genetic recombination technology.

The transformed cell was homogenized and ultra-centrifuged (100,000×g), and the centrifuged residue containing the cell membrane fraction was collected and suspended in PBS. The obtained cell membrane fraction was injected together with complete Freund's adjuvant into the foot pad of a Wistar rat for the initial immunization (day 0). In addition, the cell membrane fraction was administered as an antigen into the foot pad with intervals, on day 7, day 14, and day 28. Two days after the final immunization, lymph node cells were collected.

The lymph node cells and mouse myeloma cells PAI (JCR No. B 0113; Res. Disclosure, Vol. 217, p. 155, 1982) were mixed in a 5:1 ratio, and a monoclonal antibody-producing hybridoma was prepared by fusing the cells using polyethylene glycol 4000 (Boehringer Mannheim) as the fusing agent. Hybridoma selection was performed by culturing in a HAT-containing ASF104 medium (Ajinomoto) containing 10% fetal bovine serum and aminopterin.

The fluorescence intensities of cells stained by reacting the culture supernatants of each hybridoma with the above-mentioned recombinant mouse AILIM-expressing transfected cells and then reacting them with FITC-labeled anti-rat IgG (Cappel) were measured using the EPICS-ELITE flow cytometer to confirm the reactivity of the monoclonal antibodies produced in the culture supernatant of each hybridoma against mouse AILIM. As a result, several hybridomas that produced monoclonal antibodies having reactivity towards mouse AILIM were obtained.

One of these hybridomas was named "B10.5". This hybridoma ($10^6$ to $10^7$ cells/0.5 mL/mouse each) was injected intraperitoneally to an ICR nu/nu mouse (female, 7 to 8 weeks old). Ten to twenty days later, laparotomy was performed on the mouse under anesthesia, and a large quantity of rat anti-mouse AILIM monoclonal antibody (IgG2a) was obtained from the ascites according to standard procedures. Hereinafter, this antibody is simply referred to as "anti-AILIM antibody".

<1-3> Induction of the Inflammatory Bowel Disease

As described below, an inflammatory bowel disease (colitis) was induced by introducing CD45RB$^{high}$ into a BALB/c scid/scid mouse according to a previously reported method. Accompanying the onset and progression of the inflammatory bowel disease, a significant weight loss is known to occur 3 to 5 weeks after the introduction of CD45RB$^{high}$ T cells in this inflammatory bowel disease model.

CD4$^+$ T cells were separated and obtained from mononuclear cells derived from spleens of healthy BALB/c mice by using a MACS magnetic separation system (Miltenyi Biotec) with an anti-CD4 antibody (L3T4). More specifically, spleen cells isolated from the mice were cultured at 4° C. for 30 min with magnetic beads to which an anti-CD4 antibody is bound, and then, these cells were washed and enriched by passing through a magnetic flow column.

After labeling the obtained CD4$^+$ T cells (purity was confirmed to be 96-97% using a flow cytometer) with an anti-mouse CD4 antibody (RM4-5; PharMingen) labeled with phycoerythrin (PE), and an anti-CD4 antibody (16A; PharMingen) labeled with fluorescein isothiocyanate (FITC), they were sorted using a FACS Vantage (Becton Dickinson), and fractioned into T cells having a high expression of CD45RB (CD45RB$^{high}$) and T cells having a low expression of CD45RB (CD45RB$^{low}$).

Next, in order to induce colitis in the BALB/c scid/scid mice, the obtained CD45RB$^{high}$ T cells ($5\times10^5$ cells/200 μL PBS) were administered intraperitoneally (i.p.) to the mice.

<1-4> Administration of the Anti-AILIM Antibody

Each group of the above-mentioned SCID mice to which CD45RB$^{high}$ T cells had been introduced was treated as follows.

Group 1

The anti-AILIM antibody (250 μg/250 μL PBS) was administered intraperitoneally immediately after the introduction of CD45RB$^{high}$ T cells (first administration), and thereafter continuously every week at a frequency of 3 times/ week.

Group 2

The negative control antibody (rat IgG, Sigma, 250 μg/250 μl PBS) was administered intraperitoneally immediately after the introduction of CD45RB$^{high}$ T cells (first administration), and thereafter continuously every week at a frequency of 3 times/week. Simultaneously, after the 8th week from immediately after the introduction of CD45RB$^{high}$ T cells (first administration) and onwards, in addition to the negative control antibody, the anti-AILIM antibody (250 μg/250 μL PBS) was intraperitoneally administered continuously every week at a similar frequency.

Group 3

The negative control antibody (rat IgG, Sigma, 250 μg/250 μl PBS) was intraperitoneally administered from immediately after the introduction of CD45RB$^{high}$ T cells (first administration) and thereafter continuously every week at a frequency of 3 times/week.

The degree of progression of the inflammatory bowel disease, and the degree of the suppression and treatment of the onset and progression of the disease due to the anti-AILIM antibody were analyzed by measuring the body weight of each group over time from immediately before the introduction of T cells.

Figure 1:
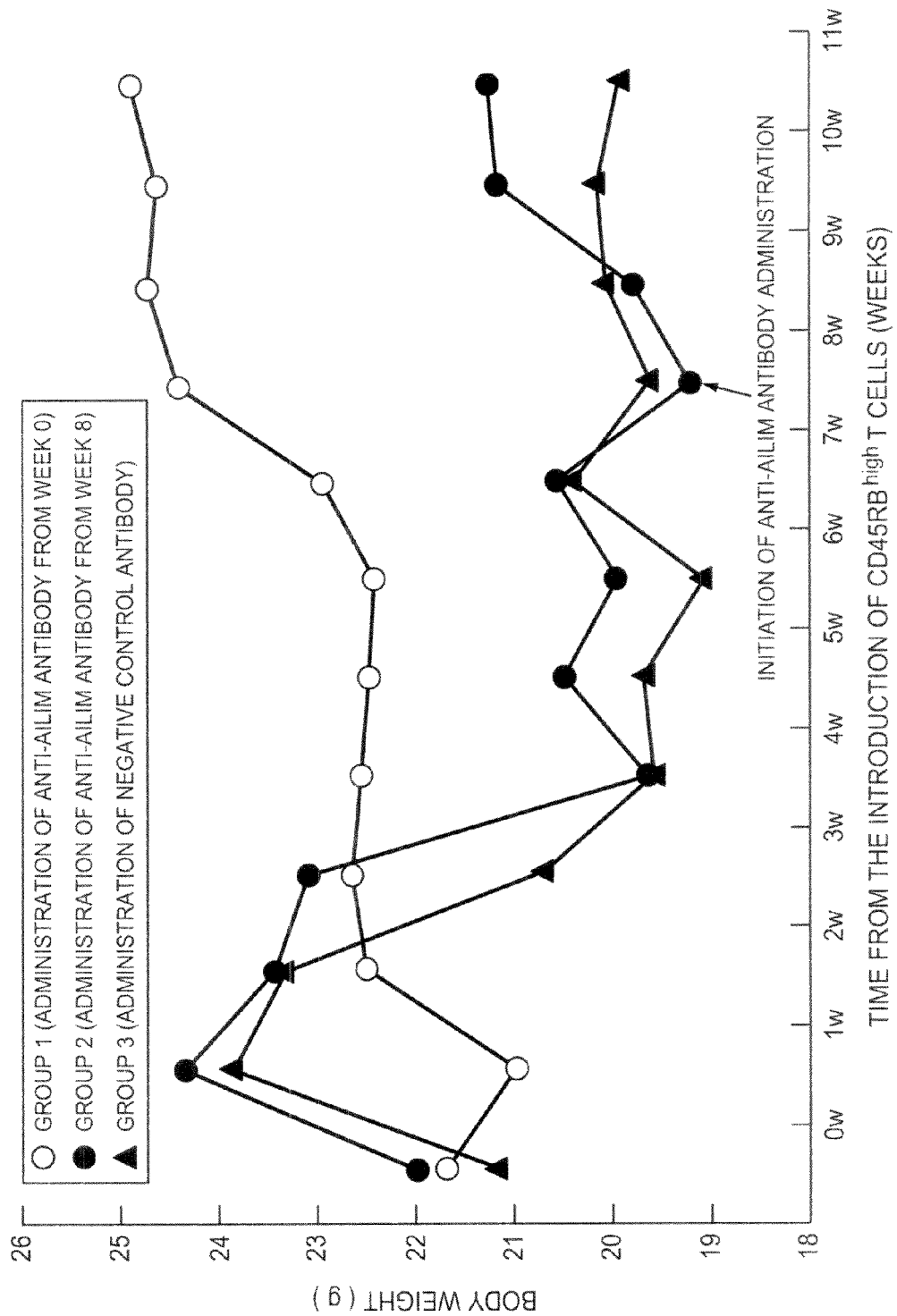
FIG. 1 shows the suppressive effect of an anti-AILIM antibody on the onset of an inflammatory bowel disease when the antibody is continuously administered (before the onset or after disease progression), and the therapeutic effect on the inflammatory bowel disease by the administration of the anti-AILIM antibody, determined using weight loss, which is a characteristic of colitis, as an index.

The results are shown in FIG. 1.

Therefore, as expected, a significant weight loss accompanying the progression of the inflammatory bowel disease occurred in the group to which only the negative control antibody was administered (Group 3). However, absolutely no weight loss was observed and the onset of inflammatory bowel disease was completely suppressed in the group to which the anti-AILIM antibody was continuously administered from immediately after the introduction of CD45RB$^{high}$ T cells (Group 1).

Furthermore, in the group to which the negative control antibody alone was administered from immediately after the introduction of CD45RB$^{high}$ T cells to week 7, and from week 8 the anti-AILIM antibody was administered in addition to the negative control antibody (Group 2), a significant increase (recovery) in body weight was observed from immediately after the initiation of anti-AILIM antibody administration, compared to the group to which only the negative control antibody alone was administered even after week 8 and onwards (Group 3). Therefore, the anti-AILIM antibody was found to cure inflammatory bowel disease.

Furthermore, the degree of progression of the inflammatory bowel disease, as well as the degree of suppression and treatment of the onset and progression of the disease by the anti-AILIM antibody were analyzed by collecting the large intestines 6 weeks after T cell introduction from some mice of Group 1 and Group 3, and examining their state with the naked eye. As a normal control, a similar observation was carried out on the large intestine collected from BALB/c scid/scid mouse to which no CD45RB$^{high}$ T cells were introduced and no antibodies were administered.

Figure 2:
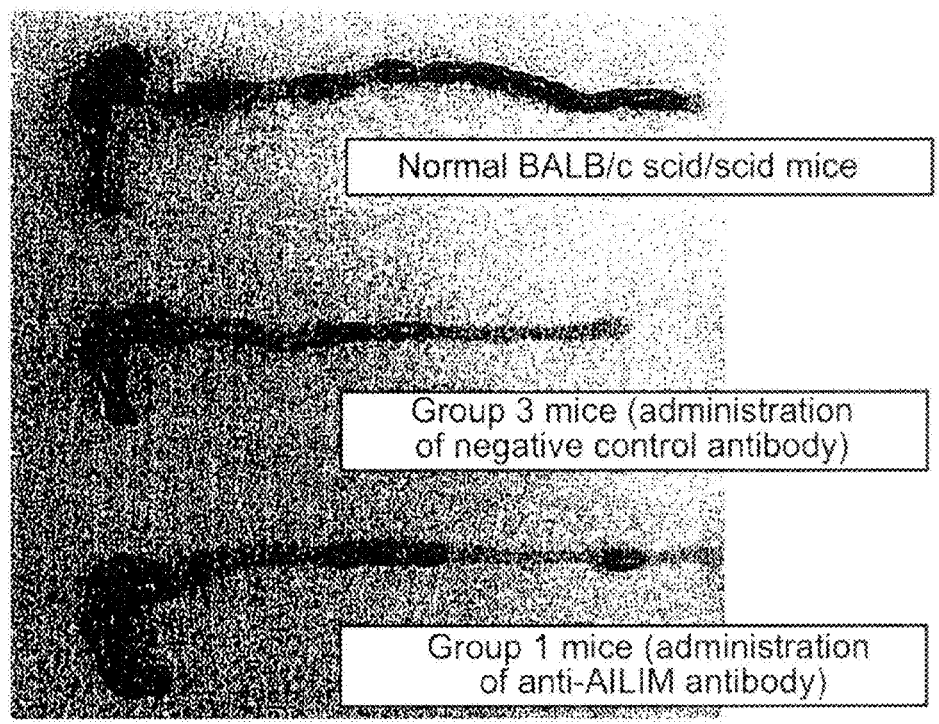
FIG. 2 is a photograph showing the state of the large intestine of normal mice that have not developed the inflammatory bowel disease, that of mice affected by the inflammatory bowel disease, and that of mice in which the onset of the inflammatory bowel disease is found to be suppressed by the administration of the anti-AILIM antibody, respectively.

The results are shown in FIG. 2.

As a result, involution of the large intestine (thickening and shortening of the intestinal tract) accompanying progression of inflammatory bowel disease, and untreated stools were observed in the group to which the negative control antibody was administered (Group 3). However, the state of the large intestine of the group to which anti-AILIM antibody was administered (Group 1) was similar to that of the large intestine of the normal control, and the anti-AILIM antibody was revealed to significantly suppress the onset and progression of inflammatory bowel disease.

Example 2

Therapeutic Effect on Inflammatory Bowel Disease in the Mouse Colitis Model <Trial 2>

<2-1> Animals

Immunodeficient BALB/c scid/scid mice, C57BL/6 scid/scid mice, and normal BALB/c mice (all male, 6 to 8 weeks old, CLEA Japan) were used.

<2-2> Monoclonal Antibodies

A monoclonal antibody against mouse AILIM (ICOS), a monoclonal antibody against mouse B7RP-1 which is a ligand of mouse AILIM (ICOS), and a negative control antibody were used.

B10.5 produced as described above was used for the anti-mouse AILIM/ICOS monoclonal antibody.

The anti-mouse B7RP-1 monoclonal antibody was produced in the following manner. An SD rat was immunized with recombinant L cells that express mouse B7RP-1 produced according to standard procedures. Spleen cells of the immunized rat were obtained, and by cell fusion with myeloma cells according to standard procedures, hybridomas were produced. Using the culture supernatant of each of the hybridomas, the degree of the binding of anti-mouse B7RP-1 monoclonal antibody contained in the culture supernatant to recombinant cells (NRK cells) that express mouse B7RP-1 was measured by EIA, and hybridomas producing an antibody that bind to mouse B7RP-1 were selected. Anti-mouse B7RP-1 monoclonal antibody used for the examination was prepared from the culture supernatant of the selected hybridomas. Furthermore, it was confirmed that the anti-mouse B7RP-1 monoclonal antibody has an activity to inhibit the binding of mouse AILIM-Ig (fusion polypeptide comprising the soluble region of mouse AILIM/ICOS and Fc of an immunoglobulin) to recombinant cells that express mouse B7RP-1.

Rat IgG (Sigma) that does not react with mouse AILIM/ICOS or B7RP-1 was used as the negative control antibody.

<2-3> Induction of Colitis (Inflammatory Bowel Disease)

The inflammatory bowel disease colitis was induced by introducing CD4$^+$ CD45RB$^{high}$ T cells into BALB/c scid/scid mice according to an existing report (J. Immunol., Vol. 164, p. 4878-4882, 2000).

CD4$^+$ T cells were separated from the spleen cells of normal BALB/c mice using the anti-CD4 (L3T4) MACS magnetic separation system (Miltenyi Biotec) following the attached instructions. The CD4$^+$ T cells (purity of 96-97%, analyzed by FACS) were labeled with a PE-labeled anti-mouse CD4 antibody (RM4-5; PharMingen) and a FITC-labeled anti-CD45RB antibody (16A; PharMingen), and were sorted into CD45RB$^{high}$ T cells and CD45RB$^{low}$ T cells using FACS Vantage (Becton Dickinson).

The inflammatory bowel disease (colitis) was induced by intraperitoneal administration of CD45RB$^{high}$ T cells (5×10$^5$ cells/200 μL PBS) into BALB/c scid/scid mice.

<2-4> Treatment of Inflammatory Colitis by the Anti-AILIM Antibody

The Anti-mouse AILIM/ICOS monoclonal antibody (250 μg/250 μL PBS), the anti-mouse B7RP-1 monoclonal antibody (250 μg/250 μL PBS), or the control antibody (250 μg/250 μL PBS) was administered intraperitoneally at a frequency of 3 times per week for 7 weeks from the time of introduction (week 0) of CD45RB$^{high}$ T cells to mice produced as described above in which inflammatory colitis was induced.

On the other hand, to investigate the therapeutic effect of the anti-AILIM/ICOS antibody under the state of progressed inflammatory colitis, the anti-AILIM/ICOS monoclonal antibody was administered (at a concentration of 250 μg/body; 3 times/week; i.p.) under conditions similar to that mentioned above from 3 weeks after the introduction of CD45RB$^{high}$ T cells to mice produced as described above in which inflammatory colitis had been induced. Seven weeks after the introduction of CD45RB$^{high}$ T cells, the test animals were sacrificed and the state of inflammation in the large intestine was analyzed.

<2-5> Introduction of Pathogenic CD4$^{30}$ T Cells from Mice with Colitis to Mice From the lamina propria (LP) of the large intestine of BALB/c scid/scid mice to which CD4$^+$ CD45RB$^{high}$ T cells had been introduced (adoptive transfer), CD4$^+$ cells (LP CD4$^+$ T cells) were isolated using the above-mentioned MACS magnetic beads 7 weeks after the introduction of the T cells. The purity of the isolated LP CD4$^+$ T cells was confirmed to be 95% or more by FACS.

The LP CD4$^+$ T cells ($1\times10^6$ cells/200 µL PBS; i.p.) were administered to BALB/c scid/scid mice. Next, the anti-AILIM/ICOS antibody (250 µg/250 µL PBS) or the negative control antibody (rat IgG; 250 µg/250 µL PBS) was administered at a frequency of 3 times per week to the test mice. Four weeks after the administration of LP CD4$^+$ T cells, the mice were euthanized, the large intestines were removed and histologically analyzed.

<2-6> Histological Examination and Immunohistochemical Staining

Large intestine tissue samples collected from each of the aforementioned test animals were immobilized in PBS containing 6% formalin. Paraffin-immobilized large intestine tissue sections (5 µm) were stained by hematoxylin and eosin (HE staining). Each of the produced tissue section specimens was analyzed. The degree of inflammation of the large intestine was converted to scores according to an existing report (Gastroenterology, Vol. 119, p. 715-723, 2000).

On the other hand, the large intestine samples for immunohistochemical staining analysis were immobilized in OCT compound, frozen in liquid nitrogen, and stored at −80° C. Staining of the tissue sections was performed by the avidin-biotin complex method.

The tissue sections (6 µm) were incubated with biotinylated anti-mouse AILIM/ICOS monoclonal antibody, biotinylated anti-mouse B7RP-1 monoclonal antibody, biotinylated anti-mouse CD4 monoclonal antibody (RM4-5; rat IgG1; PharMingen), biotinylated anti-mouse F4/80 monoclonal antibody (rat IgG2; PharMingen), or biotinylated isotype-matched control antibody (PharMingen). The biotinylated antibody was detected with streptavidin-biotinylated horseradish peroxidase complex (Vectastain ABC Kit; Vector), and was visualized with diaminobenzidine. Next, each of the sections was counter stained with hematoxylin.

<2-7> Detection of Apoptotic Cells

Apoptotic cells in frozen tissue sections were detected using the ApoTag Kit (Intergen) according to the previously reported TUNEL method. By observing under a microscope, TUNEL positive cells in the tissue sections were quantified by calculating the TUNEL positive cells in 500 lamina propria mononuclear cells (LPMC) that had infiltrated into 5 parts of one section. The percentage of TUNEL positive cells in 500 LPMC was taken to be the apoptosis index.

<2-8> Results

The results are shown in FIG. 3 to FIG. 12.

<2-8-1> Suppression of Colitis by Administration of Anti-AILIM/ICOS Antibody

In the test mice (control mice) to which the negative control antibody (rat IgG) had been administered, severe colitis developed 4 to 7 weeks after the introduction of CD45RB$^{high}$ T cells, and not only a significant weight loss (FIG. 3), but also a significant thickening of the intestinal wall of the large intestine accompanied by diarrhea and inflammation was observed.

In the control mice, the average value (on week 7) of histological scores (indicating the severity of colitis) characterized by transmural inflammation in which a large number of lymphocytes are observed in the lamina propria and submucosa, and prominent epithelial hyperplasia accompanying a decrease of goblet cells was $5.9\pm1.2$ (FIG. 4).

Figure 3:
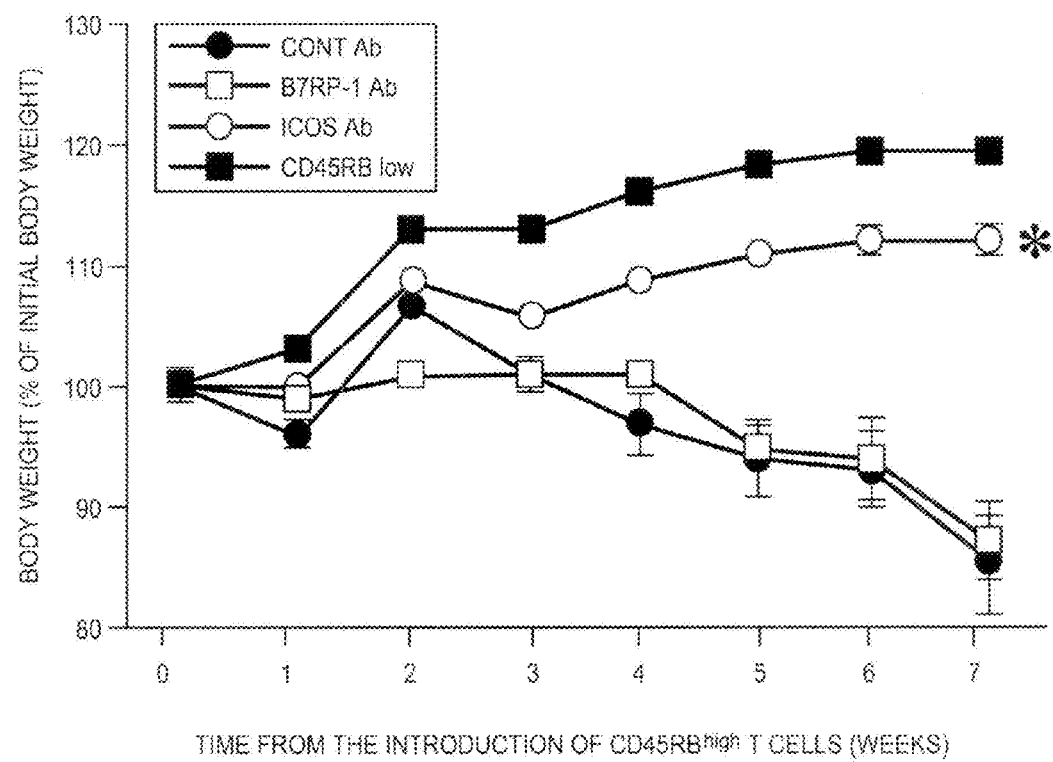
FIG. 3 shows the suppressive effect of the anti-AILIM antibody on the onset of the inflammatory bowel disease when the antibody is continuously administered, as determined using weight loss, which is a characteristic of colitis, as an index.

On the other hand, mice treated with the anti-AILIM/ICOS antibody were absolutely healthy, and signs of colitis and thickening of the colonic wall was not observed, and weight gain was observed over time (FIG. 3). Furthermore, the histological score of the colonic wall tissue was $0.8\pm0.7$ in these anti-AILIM/ICOS antibody-treated mice (n=7), and clear morbid changes could not be observed (FIG. 4).

The average number of CD4$^+$ T cells observed in the lamina propria of the large intestine of mice with colitis (control mice) that have developed an inflammation was $44\pm9\times10^5$ cells/large intestine, whereas in mice treated with the anti-AILIM/ICOS antibody, it was $21\pm3\times10^5$ cells/large intestine (p<0.01) (FIG. 5).

<2-8-2> Induction of Apoptosis in Tissue-infiltrating Mononuclear Cells by the Anti-AILIM/ICOS Antibody In the large intestine of mice to which the anti-AILIM/ICOS antibody was administered, a significant increase of apoptotic cells (most of them were tissue-infiltrating mononuclear cells) was observed compared to that in mice treated with negative control antibody (control mice).

The apoptosis index as shown by quantitative analysis of the apoptotic cells in the large intestine was significantly high in mice to which the anti-AILIM/ICOS antibody was administered (n=5) compared to that in mice to which control antibody was administered (control mouse) (FIG. 6).

These results showed that the suppressive effect on colitis due to the treatment with anti-AILIM/ICOS antibody is attributed to the depletion of pathogenic T cells that express AILIM (ICOS).

<2-8-3> Suppressive Effect on Colitis due to Administration of Anti-AILIM/ICOS Antibody after Progression of Symptoms Weight loss and infiltration of lymphocytes to the colonic tissues, i.e. wasting disease which is one of the symptoms in the above-mentioned colitis model mouse, start 3 weeks or so and 2 weeks or so after the introduction of CD$_{45}$RB$^{high}$ T cells, respectively. Therefore, as mentioned above, the administration of the anti-AILIM/ICOS antibody was initiated 3 weeks after the introduction of the T cells.

In the anti-AILIM/ICOS antibody-administered group, a significant improvement in weight loss was observed (FIG. 7) and diarrhea was not seen.

Histological analysis of the colonic tissue sections of mice from each group showed that granulomatous inflammation, lymphocytic infiltration, and thickening of the epithelium were significantly reduced in the colonic tissues of the group to which the anti-AILIM/ICOS antibody was administered, compared to that of the mice to which the negative control antibody was administered (control mice). Changes in inflammation were observed in the lamina propria, and in certain cases, in lesions accompanying a mild infiltration of lymphocytes into the submucosa, but not in the muscular layer. Furthermore, the above-mentioned histological score indicating the severity of colitis (the large intestines were collected on week 7) was significantly decreased in the group of anti-AILIM/ICOS antibody-administered mice ($1.62\pm0.81$) compared to that of the group of negative control antibody-administered mice (control mice; $5.93\pm1.23$) (p<0.05; FIG. 8). Furthermore, the number of infiltrating CD4$^+$ T cells (week 7) was significantly decreased in the anti-AILIM/ICOS antibody-administered mice ($5.50\pm0.7\times10^6$ cells) compared to that of the control mice ($31.3\pm7.7\times10^6$ cells) (p<0.05; FIG. 9).

<2-8-4> Suppressive Effect of the Anti-AILIM/ICOS Antibody on Colitis Induced by the Introduction of Lamina Propria CD4+ T Cells Derived from a Colitis Donor To investigate the therapeutic effect of anti-AILIM/ICOS antibody on pathogenic T cells, as described above, colitis was induced by administering LP CD4$^{30}$ T cells derived from mice with colitis to BALB/c scid/scid mice, followed by the administration of the anti-AILIM/ICOS antibody.

In the anti-AILIM/ICOS antibody-administered mice, weight loss (FIG. 10) was significantly improved. In addition, the histological score indicating the severity of colitis (the large intestines were collected on week 4; FIG. 11) and infiltration of CD4+ cells into the colonic lamina propria (week 4) (FIG. 12) were also significantly decreased compared to that of the negative control antibody-administered mice (control mice).

INDUSTRIAL APPLICABILITY

The pharmaceutical compositions of the present invention (particularly preferably comprising a substance having an activity to induce cell death, apoptosis, or depletion of cells that express AILIM/ICOS) are extremely useful for suppressing, preventing, and/or treating diseases that may be caused by an abnormal immunity of the intestinal tract, more specifically, inflammatory bowel diseases (especially Crohn's disease and colitis (ulcerative colitis and such)) and alimentary allergies.

The pharmaceutical compositions of this invention can enhance the therapeutic effect on inflammatory bowel diseases and alimentary allergies when used in combination with existing pharmaceutical agents that are prescribed for the treatment of such inflammatory diseases and alimentary allergies.

Furthermore, a pharmaceutical composition comprising a human antibody against AILIM, which is included as a part of the pharmaceutical composition of this invention, is extremely useful as a drug since it does not cause any side effects such as allergies as seen when administering antibodies derived from mice to humans.

The invention claimed is:

1. A method of suppressing or treating an inflammatory bowel disease in a subject, the method comprising administering to the subject an effective amount of a composition comprising (a) an antibody or a portion thereof that binds to human AILIM, and (b) a pharmaceutically acceptable carrier.

2. The method of claim 1, wherein the inflammatory bowel disease is colitis.

3. The method of claim 1, wherein the inflammatory bowel disease is Crohn's disease.

4. The method of claim 1, wherein the antibody or portion thereof is a monoclonal antibody.

5. The method of claim 4, wherein the monoclonal antibody is a chimeric monoclonal antibody, a humanized monoclonal antibody, or a human monoclonal antibody.

6. The method of claim 1, wherein the antibody or portion thereof is an F(ab')$_2$ fragment, an Fab' fragment, an Fab fragment, an Fv fragment, or a single domain antibody.

7. The method of claim 2, wherein the antibody or portion thereof is a monoclonal antibody.

8. The method of claim 7, wherein the monoclonal antibody is a chimeric monoclonal antibody, a humanized monoclonal antibody, or a human monoclonal antibody.

9. The method of claim 2, wherein the antibody or portion thereof is an F(ab')$_2$ fragment, an Fab' fragment, an Fab fragment, an Fv fragment, or a single domain antibody.

10. The method of claim 3, wherein the antibody or portion thereof is a monoclonal antibody.

11. The method of claim 10, wherein the monoclonal antibody is a chimeric monoclonal antibody, a humanized monoclonal antibody, or a human monoclonal antibody.

12. The method of claim 3, wherein the antibody or portion thereof is an F(ab')$_2$ fragment, an Fab' fragment, an Fab fragment, an Fv fragment, or a single domain antibody.

13. A method of suppressing or treating an inflammatory bowel disease in a subject, the method comprising administering to the subject an effective amount of a composition comprising (a) an antibody that binds to human AILIM, and (b) a pharmaceutically acceptable carrier.

14. The method of claim 13, wherein the inflammatory bowel disease is colitis.

15. The method of claim 13, wherein the inflammatory bowel disease is Crohn's disease.

16. The method of claim 13, wherein the antibody is a monoclonal antibody.

17. The method of claim 16, wherein the monoclonal antibody is a chimeric monoclonal antibody, a humanized monoclonal antibody, or a human monoclonal antibody.

18. The method of claim 14, wherein the antibody or portion thereof is a monoclonal antibody.

19. The method of claim 18, wherein the monoclonal antibody is a chimeric monoclonal antibody, a humanized monoclonal antibody, or a human monoclonal antibody.

20. The method of claim 15, wherein the antibody or portion thereof is a monoclonal antibody.

21. The method of claim 20, wherein the monoclonal antibody is a chimeric monoclonal antibody, a humanized monoclonal antibody, or a human monoclonal antibody.

* * * * *